United States Patent
Arnér et al.

(10) Patent No.: US 11,110,089 B2
(45) Date of Patent: Sep. 7, 2021

(54) PYRIDAZINONES AND THEIR USE IN THE TREATMENT OF CANCER

(71) Applicants: Elias Set Jenö Arnér, Stockholm (SE); THE UNITED STATES OF AMERICA, AS REPRESENTED BY THE SECRETARY, DEPARTMENT OF HEALTH AND HUMAN SERVICES, Bethesda, MD (US)

(72) Inventors: Elias Set Jenö Arnér, Stockholm (SE); William Chester Stafford, Stockholm (SE); Nathan Patrick Coussens, Vienna, VA (US); Diane Karen Luci, Germantown, MD (US); David Joseph Maloney, Point Of Rocks, MD (US); Anton Simeonov, Bethesda, MD (US); Ajit Jadhav, Chantilly, VA (US); Thomas S. Dexheimer, Lansing, MI (US)

(73) Assignees: The United States of America, as represented by the Secretary, Department of Health and Human Services, Bethesda, MD (US); Elias Set Jenö Arnér, Stockholm (SE)

( * ) Notice: Subject to any disclaimer, the term of this patent is extended or adjusted under 35 U.S.C. 154(b) by 566 days.

(21) Appl. No.: 15/750,817

(22) PCT Filed: Aug. 5, 2016

(86) PCT No.: PCT/US2016/045729
§ 371 (c)(1),
(2) Date: Feb. 6, 2018

(87) PCT Pub. No.: WO2017/027357
PCT Pub. Date: Feb. 16, 2017

(65) Prior Publication Data
US 2020/0113897 A1    Apr. 16, 2020

(30) Foreign Application Priority Data
Aug. 7, 2015  (GB) ................................. 1514015

(51) Int. Cl.
*C07D 413/06* (2006.01)
*A61K 31/501* (2006.01)
*A61K 45/06* (2006.01)

(52) U.S. Cl.
CPC ............ *A61K 31/501* (2013.01); *A61K 45/06* (2013.01); *C07D 413/06* (2013.01)

(58) Field of Classification Search
CPC ....... A61K 31/501; A61K 45/06; A61P 35/00; C07D 413/06
See application file for complete search history.

(56) References Cited

U.S. PATENT DOCUMENTS

| 4,939,140 A | 7/1990 | Larson et al. |
| 2013/0331382 A1 | 12/2013 | Hubbard et al. |

FOREIGN PATENT DOCUMENTS

| CN | 103864769 | * | 6/2014 | ........... C07D 413/06 |
| CN | 103864769 A | | 6/2014 | |
| WO | 2009/057827 A1 | | 5/2009 | |
| WO | 2009/083076 A1 | | 7/2009 | |
| WO | 2016090371 A2 | | 6/2016 | |

OTHER PUBLICATIONS

Abdel-Hakeem et al., Synthesis and Antimicrobial Activity of Some 6-(4-Fluorophenyl) Pyridazine Derivatives. Bull Fac Pharm Cairo Univ. 2007;45:39-46.
Arnér et al., Physiological functions of thioredoxin and thioredoxin reductase. Eur J Biochem. Oct. 2000;267(20):6102-9.
Arnér, Focus on mammalian thioredoxin reductases—important selenoproteins with versatile functions. Biochim Biophys Acta. Jun. 2009;1790(6):495-526.
Becker et al., Thioredoxin reductase as a pathophysiological factor and drug target. Eur J Biochem. Oct. 2000;267(20):6118-25.
Cox et al., The thioredoxin reductase inhibitor auranofin triggers apoptosis through a Bax/Bak-dependent process that involves peroxiredoxin 3 oxidation. Biochemical Pharmacology. 2008;76:1097-1109.
Fath et al., Enhancement of carboplatin-mediated lung cancer cell killing by simultaneous disruption of glutathione and thioredoxin metabolism. Clin Cancer Res. Oct. 1, 2011;17(19):6206-17.
Harris et al., Glutathione and thioredoxin antioxidant pathways synergize to drive cancer initiation and progression. Cancer Cell. Feb. 9, 2015;27(2):211-22.
Hashemy et al., Motexafin gadolinium, a tumor-selective drug targeting thioredoxin reductase and ribonucleotide reductase. J Biol Chem. Apr. 21, 2006;281(16):10691-7.
Krisfinamurthy et al., Gold(I)-mediated inhibition of protein tyrosine phosphatases: a detailed in vitro and cellular study. J Med Chem. Aug. 14, 2008;51(15):4790-5.
Lillig et al., Glutaredoxin systems. Biochim Biophys Acta. Nov. 2008;1780(11):1304-17.

(Continued)

*Primary Examiner* — Erich A Leeser
(74) *Attorney, Agent, or Firm* — McCarter & English, LLP; Steven G. Davis; Mei Bai

(57) ABSTRACT

There is provided compounds of formula (I) or pharmaceutically-acceptable salts thereof, wherein W, X, Y, Z, $R^1$, $R^2$ and $R^3$ have meanings provided in the description, which compounds are useful in the treatment of cancers.

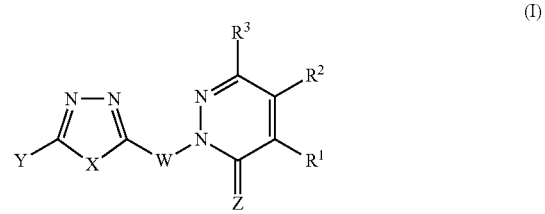

(I)

15 Claims, 1 Drawing Sheet

(56) References Cited

OTHER PUBLICATIONS

Luo et al., Principles of cancer therapy: oncogene and non-oncogene addiction. Cell. Mar. 6, 2009;136(5):823-37.
Mandal et al., Loss of thioredoxin reductase 1 renders tumors highly susceptible to pharmacologic glutathione deprivation. Cancer Res. Nov. 15, 2010;70(22):9505-14.
Prigge et al., Hepatocyte DNA replication in growing liver requires either glutathione or a single allele of txnrd1. Free Radic Biol Med. Feb. 15, 2012;52(4):803-10.
Rigobello et al., Effect of auranofin on the mitochondrial generation of hydrogen peroxide. Role of thioredoxin reductase. Free Radic Res. Jul. 2005;39(7):687-95.
Trachootham et al., Targeting cancer cells by ROS-mediated mechanisms: a radical therapeutic approach? Nat Rev Drug Discov. Jul. 2009;8(7):579-91.
El-Hashash et al., "Synthesis of novel heterocyclic compounds with expected antibacterial activities from 4-(4-bromophenyl) . . . " J. Hetero. Chem, vol. 52:732-743, May 31, 2014.
International Search Report and Written Opinion, PCT/US2016/045729, dated Oct. 21, 2016.

\* cited by examiner

PYRIDAZINONES AND THEIR USE IN THE TREATMENT OF CANCER

RELATED APPLICATIONS

This application is a 35 U.S.C. § 371 national stage filing of International Application No. PCT/US2016/045729, filed on Aug. 5, 2016, which claims the benefit of priority to United Kingdom Patent Application No. 1514015.5, filed on 7 Aug. 2015. The entire contents of each of the foregoing applications are hereby incorporated herein by reference in their entirety.

FIELD OF THE INVENTION

The present invention relates to novel compounds and compositions comprising the same, and their use in the treatment of cancer. In particular, the invention relates to compounds, compositions and methods for the treatment of cancers through specific and potent inhibition of thioredoxin reductase without targeting of glutathione reductase.

BACKGROUND OF THE INVENTION

The listing or discussion of an apparently prior-published document in this specification should not necessarily be taken as an acknowledgement that the document is part of the state of the art or is common general knowledge.

Although the increased understanding of the role of oncogenes, and the development of new anticancer treatments and diagnosis, have improved the life expectancy of cancer patients, there is still a high medical need to find more effective and less toxic treatments for cancers, such as breast cancer, head and neck cancer, melanoma, leukaemia, and colon and lung cancer.

It is well known that excessive production of reactive oxygen species is a common feature of cancer cells due to their distorted metabolism and exaggerated replicative drive. Cancer cells are able to survive their unnaturally high production of reactive oxygen species through concomitant upregulation of robust antioxidant defense mechanisms.

Radiotherapy and chemotherapy protocols compete against antioxidant defense mechanisms, further increasing reactive oxygen species levels beyond adapted thresholds through targeting of multiple cellular compartments and targets. Thus, sensitization of cancer cells to their endogenous reactive oxygen species production can additionally induce cancer cell death. In contrast, normal cells have reserved capacity to combat oxidative stress.

With this in mind, it has been suggested that if reactive oxygen species levels could be further increased, or the cellular defenses against reactive oxygen species could be deliberately impaired, these systems may serve to allow for a possible therapeutic mechanism of action for anticancer therapy (Luo, J., Solimini, N. L. & Elledge, S. J., *Cell*, 136, 823 (2009); Trachootham, D., Alexandre, J. & Huang, P., *Nat Rev Drug Discov*, 8, 579 (2009)).

Increased tolerance to oxidative stress of cancer cells can occur through activation of the two major antioxidant systems in human and other mammals, the glutathione and thioredoxin systems. Concomitant inhibition of the glutathione and thioredoxin systems therefore has been proposed as a mechanism for anticancer activity (Harris, I. S., et al., *Cancer Cell* 27, 211 (2015); Mandal, P. K., et al., *Cancer Res*, 70, 9505-9514 (2010); Fath, M. A., Ahmad, I. M., Smith, C. J., Spence, J. & Spitz, D. R., *Clin Cancer Res.*, 17, 6206 (2011)).

Cytosolic thioredoxin reductase is a key enzyme for the whole cytosolic thioredoxin system, which in turn is responsible for a cascade of signalling events and antioxidant activities (Arnér, E. S. J., *Biochim Biophys Acta*, 1790, 495-526 (2009)). A high expression level of cytosolic thioredoxin reductase in various cancers correlates to a more severe cancer phenotype, chemotherapeutic drug resistance, and poor prognosis.

However, as normal, non-cancerous cells require either the glutathione or the thioredoxin systems for survival (Arnér, E. S. & Holmgren, A., *Eur J Biochem*, 267, 6102 (2000); Lillig, C. H., Berndt, C. & Holmgren, A., *Biochim Biophys Acta*, 1780, 1304 (2008); Prigge, J. R., et al., *Free Radic Biol Med*, 52, 803 (2012)), it is difficult to therapeutically target both of these antioxidant systems without triggering major unwanted toxicities.

It has been suggested that several chemotherapeutic protocols for anticancer treatment involve inhibition of cytosolic thioredoxin reductase together with other components of the cell (Becker, K. et al. *Eur. J. Biochem.*, 267, 6118 (2000)). For example, motexafin gadolinium, marketed as a radiosensitizing drug and thioredoxin reductase inhibitor, is also a potent ribonucleotide reductase inhibitor (Hashemy, S. I., Ungerstedt, J. S., Zahedi Avval, F. & Holmgren, A., *J Biol Chem*, 281, 10691 (2006)). Auranofin, a potent thioredoxin reductase inhibitor, concomitantly localizes to and damages the mitochondria (Cox, A. G., Brown, K. K., Arnér, E. S. & Hampton, M. B., *Biochem Pharmacol*, 76, 1097-1109 (2008); Krishnamurthy, D., et al., *J Med Chem*, 51, 4790 (2008); Rigobello, M. P., Folda, A., Baldoin, M. C., Scutari, G. & Bindoli, A., *Free Radic Res*, 39, 687 (2005)).

The present innovation relates to the development and usage of novel compounds specifically and potently targeting cytosolic thioredoxin reductase, without targeting the closely related flavoprotein glutathione reductase that supports the function of the glutathione system, as a means of obtaining a new efficient anticancer treatment that at the same time presents limited toxic side effects.

In particular, the inventors have unexpectedly found that novel, pyridazinone compounds may achieve highly selective inhibition of cytosolic thioredoxin reductase by acting as selective and potent inhibitors of the enzyme without causing inhibition of glutathione reductase.

Specifically, by potently inhibiting thioredoxin reductase selectively over glutathione reductase, the novel pyridazinones have the potential to be effective against cancer forms having dysfunctional redox status, with minimal general toxic effects to normal cells. Such inhibitors may also be a suitable adjuvant therapy to be used in conjunction with radiotherapies or other chemotherapeutic approaches. Based on these surprising results, the present invention aims to provide new treatments for cancers.

Chinese patent application CN 103864769 claims certain oxadiazole-3-pyridazinones, which are suggested to be useful as insecticides.

El-Hashash, M. A. et al., J Het Chem, 52, 732 (2015) and Abdel-Hakeem, M. et al., *Bull Faculty Pharm (Cairo)*, 45, 39 (2007) describe certain oxadiazole-3-pyridazinones, which have been evaluated as antibiotics. However, such compounds have an essential 4-flurophenyl or 4-bromophenyl substituent in the 6-positon of the pyridazinone.

DETAILED DESCRIPTION OF THE INVENTION

It has now been found that certain pyridazinones have surprising properties that render them useful in the treatment of cancers.

Compounds of the Invention

In a first aspect of the invention, there is provided a compound of formula I

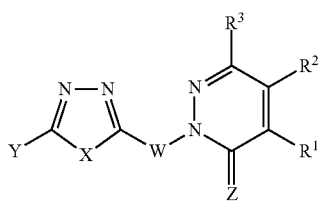

or a pharmaceutically acceptable salt thereof, wherein:
W represents $C_1$ alkylene optionally substituted by one or more groups independently selected from $R^4$;
X represents O or S;
Y represents $C_{1-6}$ alkyl optionally substituted by one or more groups independently selected from $G^{1a}$, heterocycloalkyl optionally substituted by one or more groups independently selected from $G^{1b}$, aryl optionally substituted by one or more groups independently selected from $G^{1c}$, or heteroaryl optionally substituted by one or more groups independently selected from $G^{1d}$;
Z represents O, S or $NR^5$;
$R^1$ represents H, halo, $R^{a1}$, —CN, —C($Q^{a1}$)$R^{b1}$, —C($Q^{b1}$)N($R^{c1}$)$R^{d1}$, —C($Q^{c1}$)$OR^{e1}$, —S(O)$_n$$R^{f1}$, —S(O)$_p$N($R^{g1}$)$R^{h1}$, —S(O)$_p$$OR^{i1}$ or —$NO_2$;
$R^2$ represents H, halo, —CN or —$N_3$;
$R^3$ represents H, halo or $R^{j1}$;
$R^4$ represents halo or $C_{1-6}$ alkyl optionally substituted by one or more groups independently selected from $G^{1e}$;
$R^5$ represents H, $R^{k1}$, —$OR^{l1}$ or —N($R^{m1}$)$R^{n1}$;
$Q^{a1}$ to $Q^{c1}$ each independently represents =O, =S, =$NR^{o1}$ or =N($OR^{p1}$);
each $R^{a1}$, $R^{f1}$, $R^{j1}$ and $R^{k1}$ independently represents $C_{1-6}$ alkyl optionally substituted by one or more groups independently selected from $G^{2a}$, or heterocycloalkyl optionally substituted by one or more groups independently selected from $G^{2b}$;
each $R^{b1}$, $R^{c1}$, $R^{d1}$, $R^{e1}$, $R^{g1}$, $R^{h1}$, $R^{i1}$, $R^{l1}$, $R^{m1}$, $R^{n1}$, $R^{o1}$ and $R^{p1}$ independently represents H, $C_{1-6}$ alkyl optionally substituted by one or more groups independently selected from $G^{2a}$, or heterocycloalkyl optionally substituted by one or more groups independently selected from $G^{2b}$;
or any two $R^{c1}$ and $R^{d1}$, $R^{g1}$ and $R^{h1}$ and/or $R^{m1}$ and $R^{n1}$ are linked together to form, along with the nitrogen atom to which they are attached, a 3- to 6-membered ring, which ring optionally contains one further heteroatom and which ring optionally is substituted by one or more groups independently selected from halogen, $C_{1-3}$ alkyl optionally substituted by one or more halogens, and =O;
each $G^{1a}$, $G^{1b}$, $G^{1c}$ and $G^{1d}$ represent halogen, $R^{a2}$, —CN, -$A^{a1}$-C($Q^{a2}$)$R^{b2}$, -$A^{b1}$-C($Q^{b2}$)N($R^{c2}$)$R^{d2}$, -$A^{c1}$-C($Q^{c2}$)$OR^{e2}$, -$A^{d1}$-S(O)$_q$$R^{f2}$, -$A^{e1}$-S(O)$_q$C(O)$R^{g2}$, -$A^{f1}$-S(O)$_q$N($R^{h2}$)$R^{i2}$, -$A^{g1}$-S(O)$_q$$OR^{j2}$, —$N_3$, —N($R^{k2}$)$R^{l2}$, —N(H)CN, —$NO_2$, —$OR^{m2}$, —$SR^{n2}$ or =$Q^{d2}$;

$A^{a1}$ to $A^{g1}$ each independently represents a single bond, —N($R^6$)—, —C($Q^{e2}$)N($R^7$)— or —O—;
$Q^{a2}$ to $Q^{e2}$ each independently represents =O, =S, =$NR^{o2}$ or =N($OR^{p2}$);
each $R^6$ and $R^7$ independently represents H or $C_{1-6}$ alkyl optionally substituted by one or more F;
each $R^{a2}$ and $R^{f2}$ independently represents $C_{1-6}$ alkyl optionally substituted by one or more groups independently selected from $G^{3a}$ or heterocycloalkyl optionally substituted by one or more groups independently selected from $G^{3b}$;
each $R^{b2}$, $R^{c2}$, $R^{d2}$, $R^{e2}$, $R^{g2}$, $R^{h2}$, $R^{i2}$, $R^{j2}$, $R^{k2}$, $R^{l2}$, $R^{m2}$, $R^{n2}$, $R^{o2}$ and $R^{p2}$ independently represents H, $C_{1-6}$ alkyl optionally substituted by one or more groups independently selected from $G^{3a}$ or heterocycloalkyl optionally substituted by one or more groups independently selected from $G^{3b}$; or any two $R^{c2}$ and $R^{d2}$, $R^{h2}$ and $R^{i2}$ and/or $R^{k2}$ and $R^{l2}$ are linked together to form, along with the nitrogen atom to which they are attached, a 3- to 6-membered ring, which ring optionally contains one further heteroatom and which ring optionally is substituted by one or more groups independently selected from halogen, $C_{1-3}$ alkyl optionally substituted by one or more halogens, and =O;
each $G^{1e}$ independently represents halo, $R^{a2}$, —CN, —N($R^{a3}$)$R^{b3}$, —$OR^{c3}$ or —$SR^{d3}$;
$R^{a3}$, $R^{b3}$, $R^{c3}$ and $R^{d3}$ each independently represents H or $C_{1-6}$ alkyl optionally substituted by one or more F;
or $R^{a3}$ and $R^{b3}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, and =O;
each $G^{2a}$ and $G^{2b}$ independently represents halo, —CN, —N($R^{a4}$)$R^{b4}$, —$OR^{c4}$, —$SR^{d4}$ or =O;
each $R^{a4}$, $R^{b4}$, $R^{c4}$ and $R^{d4}$ independently represents H or $C_{1-6}$ alkyl optionally substituted by one or more F;
or $R^{a4}$ and $R^{b4}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, and =O;
each $G^{3a}$ and $G^{3b}$ independently represents halo, —CN, —N($R^{a5}$)$R^{b5}$, —$OR^{c5}$, —$SR^{d5}$ or =O;
each $R^{a5}$, $R^{b5}$, $R^{c5}$ and $R^{d5}$ independently represents H or $C_{1-6}$ alkyl optionally substituted by one or more fluoro;
or $R^{a5}$ and $R^{b5}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, and =O;
each n independently represents 0, 1 or 2,
each p independently represents 1 or 2,
each q independently represents 1 or 2,
which compounds may be referred to herein as compounds of the invention.

The skilled person will understand that references herein to compounds of the invention will include references to all embodiments and particular forms thereof.

Unless indicated otherwise, all technical and scientific terms used herein have the same meaning as commonly understood by one of ordinary skill in the art to which this invention pertains.

Pharmaceutically-acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Particular acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxy-benzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulphonate salts (e.g. benzenesulphonate, methyl-, bromo- or chloro-benzenesulphonate, xylenesulphonate, methanesulphonate, ethanesulphonate, propanesulphonate, hydroxyethanesulphonate, 1- or 2-naphthalene-sulphonate or 1,5-naphthalene-disulphonate salts) or sulphate, pyrosulphate, bisulphate, sulphite, bisulphite, phosphate, monohydrogenphosphate, dihydrogenphosphate, metaphosphate, pyrophosphate or nitrate salts, and the like.

Particular base addition salts that may be mentioned include salts formed with alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

For the avoidance of doubt, compounds of the invention may exist as solids, and thus the scope of the invention includes all amorphous, crystalline and part crystalline forms thereof, and may also exist as oils. Where compounds of the invention exist in crystalline and part crystalline forms, such forms may include solvates, which are included in the scope of the invention. Compounds of the invention may also exist in solution.

Compounds of the invention may contain double bonds and may thus exist as E (entgegen) and Z(zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution); for example, with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

As used herein, references to halo and/or halogen will independently refer to fluoro, chloro, bromo and iodo (for example, fluoro and chloro).

Unless otherwise specified, $C_{1-z}$ alkyl groups (where z is the upper limit of the range) defined herein may be straight-chain or, when there is a sufficient number (i.e. a minimum of two or three, as appropriate) of carbon atoms, be branched-chain, and/or cyclic (so forming a $C_{3-z}$-cycloalkyl group). When there is a sufficient number (i.e. a minimum of four) of carbon atoms, such groups may also be part cyclic. Part cyclic alkyl groups that may be mentioned include cyclopropylmethyl and cyclohexylethyl. When there is a sufficient number of carbon atoms, such groups may also be multicyclic (e.g. bicyclic or tricyclic) or spirocyclic. Such alkyl groups may also be saturated or, when there is a sufficient number (i.e. a minimum of two) of carbon atoms, be unsaturated (forming, for example, a $C_{2-z}$ alkenyl or a $C_{2-z}$ alkynyl group).

Unless otherwise specified, $C_{1-z}$ alkylene groups (where z is the upper limit of the range) defined herein may (in a similar manner to the definition of $C_{1-z}$ alkyl) be straight-chain or, when there is a sufficient number (i.e. a minimum of two or three, as appropriate) of carbon atoms, be branched-chain, and/or cyclic (so forming a $C_{3-z}$-cycloalkylene group).

When there is a sufficient number (i.e. a minimum of four) of carbon atoms, such groups may also be part cyclic. When there is a sufficient number of carbon atoms, such groups may also be multicyclic (e.g. bicyclic or tricyclic) or spirocyclic. Such alkylene groups may also be saturated or, when there is a sufficient number (i.e. a minimum of two) of carbon atoms, be unsaturated (forming, for example, a $C_{2-z}$ alkenylene or a $C_{2-z}$ alkynylene group). Particular alkylene groups that may be mentioned include those that are straight-chained or cyclic and saturated.

As used herein, the term heterocycloalkyl may refer to non-aromatic monocyclic and bicyclic heterocycloalkyl groups (which groups may further be bridged) in which at least one (e.g. one to four) of the atoms in the ring system is other than carbon (i.e. a heteroatom), and in which the total number of atoms in the ring system is between three and twelve (e.g. between five and ten and, most preferably, between three and eight, e.g. a 5- or 6-membered heterocycloalkyl group). Further, such heterocycloalkyl groups may be saturated or unsaturated containing one or more double and/or triple bonds, forming for example a $C_{2-z}$ (e.g. $C_{4-z}$) heterocycloalkenyl (where z is the upper limit of the range) or a $C_{7-z}$ heterocycloalkynyl group. $C_{2-z}$ heterocycloalkyl groups that may be mentioned include 7-azabicyclo-[2.2.1]heptanyl, 6-azabicyclo[3.1.1]heptanyl, 6-azabicyclo[3.2.1]-octanyl, 8-azabicyclo[3.2.1]octanyl, aziridinyl, azetidinyl, 2,3-dihydroisothiazolyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, isothiazolidinyl, morpholinyl, 7-oxabicyclo[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulpholanyl, 3-sulpholenyl, tetrahydropyranyl, tetrahydrofuryl, tetrahydropyridyl (such as 1,2,3,4-tetrahydropyridyl and 1,2,3,6-tetrahydropyridyl), thietanyl, thiiranyl, thiolanyl, tetrahydrothiopyranyl, thiomorpholinyl, trithianyl (including 1,3,5-trithianyl), tropanyl and the like. Substituents on heterocycloalkyl groups may, where appropriate, be located on any atom in the ring system including a heteroatom. Further, in the case where the substituent is another cyclic compound, then the cyclic compound may be attached through a single atom on the heterocycloalkyl group, forming a so-called "spiro"-compound. The point of attachment of heterocycloalkyl groups may be via any atom in the ring system including (where appropriate) a further heteroatom (such as a nitrogen atom), or an atom on any fused carbocyclic ring that may be present as part of the ring system. Heterocycloalkyl groups may also be in the N- or S-oxidised form.

At each occurrence when mentioned herein, particular heterocycloalkyl groups that may be mentioned include 3- to 8-membered heterocycloalkyl groups (e.g. a 4- to 6-membered heterocycloalkyl group).

As used herein, the term aryl includes references to $C_{6-14}$ (e.g. $C_{6}$-10) aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl and the like, such as phenyl). For the avoidance of doubt, the point of attachment of substituents on aryl groups may be via any carbon atom of the ring system.

As used herein, the term heteroaryl (or heteroaromatic) includes references to 5- to 14- (e.g. 5- to 10-) membered heteroaromatic groups containing one or more heteroatoms selected from oxygen, nitrogen and/or sulphur. Such heteroaryl groups may comprise one, two, or three rings, of which at least one is aromatic. Substituents on heteroaryl/heteroaromatic groups may, where appropriate, be located on any atom in the ring system including a heteroatom. The point of attachment of heteroaryl/heteroaromatic groups may be via any atom in the ring system including (where appropriate) a heteroatom. Bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocycloalkyl ring. Examples of heteroaryl/heteroaromatic groups that may be mentioned include pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, imidazothiazolyl, thienothiophenyl, pyrimidinyl, furopyridinyl, indolyl, azaindolyl, pyrazinyl, pyrazolopyrimidinyl, indazolyl, pyrimidinyl, quinolinyl, isoquinolinyl, quinazolinyl, benzofuranyl, benzothiophenyl, benzoimidazolyl, benzoxazolyl, benzothiazolyl, benzotriazolyl and purinyl. The oxides of heteroaryl/heteroaromatic groups are also embraced within the scope of the invention (e.g. the N-oxide). As stated above, heteroaryl includes polycyclic (e.g. bicyclic) groups in which one ring is aromatic (and the other may or may not be aromatic). Hence, other heteroaryl groups that may be mentioned include e.g. benzo[1,3]dioxolyl, benzo[1,4]dioxinyl, dihydrobenzo[d]isothiazole, 3,4-dihydrobenz[1,4]oxazinyl, dihydrobenzothiophenyl, indolinyl, 5H,6H,7H-pyrrolo[1,2-b]pyrimidinyl, 1,2,3,4-tetrahydroquinolinyl, thiochromanyl and the like.

For the avoidance of doubt, as used herein, references to heteroatoms will take their normal meaning as understood by one skilled in the art. Particular heteroatoms that may be mentioned include phosphorus, selenium, tellurium, silicon, boron, oxygen, nitrogen and sulphur (e.g. oxygen, nitrogen and sulphur).

For the avoidance of doubt, references to polycyclic (e.g. bicyclic) groups (e.g. when employed in the context of heterocycloalkyl groups) will refer to ring systems wherein more than two scissions would be required to convert such rings into a straight chain, with the minimum number of such scissions corresponding to the number of rings defined (e.g. the term bicyclic may indicate that a minimum of two scissions would be required to convert the rings into a straight chain). For the avoidance of doubt, the term bicyclic (e.g. when employed in the context of heterocycloalkyl groups) may refer to groups in which the second ring of a two-ring system is formed between two adjacent atoms of the first ring, and may also refer to groups in which two non-adjacent atoms are linked by either an alkylene or heteroalkylene chain (as appropriate), which later groups may be referred to as bridged.

For the avoidance of doubt, when an aryl or an heteroaryl group is substituted with a group via a double bond, such as =O, it is understood that the aryl or heteroaryl group is partly aromatic, i.e. the aryl or heteroaryl group consists of at least two rings where at least one ring is not aromatic.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. in which one or more hydrogen atoms are replaced by the hydrogen isotope deuterium.

For the avoidance of doubt, in cases in which the identity of two or more substituents in a compound of the invention may be the same, the actual identities of the respective substituents are not in any way interdependent. For example, in the situation in which two $R^4$ groups are present, those $R^4$ groups may be the same or different. Similarly, where two $R^4$ groups are present and each represent halo, the halo groups in question may be the same or different. Likewise, when more than one $R^{a1}$ is present and each independently represents $C_{1-6}$ alkyl substituted by one or more $G^{2a}$ group, the identities of each $G^{2a}$ are in no way interdependent.

For the avoidance of doubt, when a term such as "$A^{a1}$ to $A^{g1}$" is employed herein, this will be understood by the skilled person to mean $A^{a1}$, $A^{b1}$, $A^{c1}$, $A^{d1}$, $A^{e1}$, $A^{f1}$ and $A^{g1}$ inclusively. Unless otherwise stated, the same reasoning will apply to other such terms used herein.

The skilled person will appreciate that compounds of the invention that are the subject of this invention include those that are stable. That is, compounds of the invention include those that are sufficiently robust to survive isolation, e.g. from a reaction mixture, to a useful degree of purity.

All embodiments of the invention and particular features mentioned herein may be taken in isolation or in combination with any other embodiments and/or particular features mentioned herein (hence describing more particular embodiments and particular features as disclosed herein) without departing from the disclosure of the invention.

In a particular embodiment of the first aspect of the invention, there is provided a compound of formula I or a pharmaceutically acceptable salt thereof but with the proviso(s) that the compound of formula I is not:

(A) a compound as exemplified in publication CN 103864769 (including all such compounds in their free base or free acid (i.e. non-salt) form), e.g. the compound of formula I is not a compound selected from 4,5-dichloro-2-((5-(4-chlorophenyl)-1,3,4-oxadiazol-2-yl)methyl)pyridazin-3(2H)-one,
4,5-dichloro-2-((5-phenyl-1,3,4-oxadiazol-2-yl)methyl)pyridazin-3(2H)-one,
4,5-dichloro-2-((5-(p-tolyl)-1,3,4-oxadiazol-2-yl)methyl)pyridazin-3(2H)-one,
4,5-dichloro-2-(1-(5-(4-chlorophenyl)-1,3,4-oxadiazol-2-yl)propyl)pyridazin-3(2H)-one,
4,5-dichloro-2-(1-(5-phenyl-1,3,4-oxadiazol-2-yl)propyl)pyridazin-3(2H)-one,
4,5-dichloro-2-(1-(5-(p-tolyl)-1,3,4-oxadiazol-2-yl)propyl)pyridazin-3(2H)-one, and
4,5-dichloro-2-(1-(5-(4-methoxyphenyl)-1,3,4-oxadiazol-2-yl)propyl)pyridazin-3(2H)-one;

and/or (e.g. and)

(B) a compound selected from 2-((5-(thiophen-2-yl)-1,3,4-oxadiazol-2-yl)methyl)-6-(trifluoromethyl)pyridazin-3(2-H)-one,
4,5-dibromo-2-((5-methyl-1,3,4-oxadiazol-2-yl)methyl)pyridazin-3(2H)-one,
5-iodo-2-((5-methyl-1,3,4-oxadiazol-2-yl)methyl)pyridazin-3(2H)-one,
2-((5-ethyl-1,3,4-oxadiazol-2-yl)methyl)-5-iodopyridazin-3(2H)-one,
4,5-dichloro-2-((5-ethyl-1,3,4-oxadiazol-2-yl)methyl)pyridazin-3(2H)-one,
4,5-dibromo-2-((5-ethyl-1,3,4-oxadiazol-2-yl)methyl)pyridazin-3(2H)-one,
4,5-dichloro-2-((5-methyl-1,3,4-oxadiazol-2-yl)methyl)pyridazin-3(2H)-one,
2-((5-(tert-butyl)-1,3,4-oxadiazol-2-yl)methyl)-4,5-dichloropyridazin-3(2H)-one,
2-((5-isopropyl-1,3,4-oxadiazol-2-yl)methyl)-6-(trifluoromethyl)pyridazin-3(2-H)-one,
6-(tert-butyl)-2-((5-(4-chlorophenyl)-1,3,4-oxadiazol-2-yl)methyl)pyridazin-3(2H)-one,
2-((5-(3-methoxyphenyl)-1,3,4-oxadiazol-2-yl)methyl)-6-methylpyridazin-3(2H)-one,
6-methyl-2-((5-(4-nitrophenyl)-1,3,4-oxadiazol-2-yl)methyl)pyridazin-3(2H)-one,
5,6-diethyl-2-((5-isopropyl-1,3,4-oxadiazol-2-yl)methyl)-3-oxo-2,3-dihydropyridazine-4-carbonitrile,
2-((5-(4-bromophenyl)-1,3,4-oxadiazol-2-yl)methyl)-5,6-diethyl-3-oxo-2,3-dihydropyridazine-4-carbonitrile,
4,5-dichloro-2-((5-(4-nitrophenyl)-1,3,4-oxadiazol-2-yl)methyl)pyridazin-3(2)-one,
4,5-dichloro-2-((5-(3,4,5-trimethoxyphenyl)-1,3,4-oxadiazol-2-yl)methyl)pyridazin-3(2H)-one,
2-((5-cyclopropyl-1,3,4-oxadiazol-2-yl)methyl)-5,6-diethyl-3-oxo-2,3-dihydropyridazine-4-carbonitrile,
6-cyclopropyl-2-((5-ethyl-1,3,4-oxadiazol-2-yl)methyl)-4-(trifluoromethyl)pyridazin-3(2H)-one,
2-((5-(tert-butyl)-1,3,4-oxadiazol-2-yl)methyl)-6-cyclopropyl-4-(trifluoromethyl)pyridazin-3(2H)-one,
6-cyclopropyl-2-((5-methyl-1,3,4-oxadiazol-2-yl)methyl)-4-(trifluoromethyl)pyridazin-3(2H)-one,
6-cyclopropyl-2-((5-cyclopropyl-1,3,4-oxadiazol-2-yl)methyl)-4-(trifluoromethyl)pyridazin-3(2H)-one,
5,6-dimethyl-2-((5-(4-nitrophenyl)-1,3,4-oxadiazol-2-yl)methyl)-3-oxo-2,3-dihydropyridazine-4-carbonitrile,
5,6-dimethyl-3-oxo-2-((5-(3,4,5-trimethoxyphenyl)-1,3,4-oxadiazol-2-yl)methyl)-2,3-dihydropyridazine-4-carbonitrile,
2-((5-(4-bromophenyl)-1,3,4-oxadiazol-2-yl)methyl)-6-cyclopropyl-4-(trifluoromethyl)pyridazin-3(2H)-one,
2-((5-(3-bromophenyl)-1,3,4-oxadiazol-2-yl)methyl)-6-cyclopropyl-4-(trifluoromethyl)pyridazin-3(2H)-one,
6-cyclopropyl-4-(trifluoromethyl)-2-((5-(3,4,5-trimethoxyphenyl)-1,3,4-oxadiazol-2-yl)methyl)pyridazin-3(2H)-one,
2-((5-(3-bromophenyl)-1,3,4-oxadiazol-2-yl)methyl)-4,5-dichloropyridazin-3(2)-one,
4,5-dichloro-2-((5-(4-methoxyphenyl)-1,3,4-oxadiazol-2-yl)methyl)pyridazin-3(2)-one,
2-((5-(5-bromofuran-2-yl)-1,3,4-oxadiazol-2-yl)methyl)-4,5-dichloropyridazin-3(2)-one,
5,6-dimethyl-3-oxo-2-((5-phenyl-1,3,4-oxadiazol-2-yl)methyl)-2,3-dihydropyridazine-4-carbonitrile,
2-((5-(4-methoxyphenyl)-1,3,4-oxadiazol-2-yl)methyl)-5,6-dimethyl-3-oxo-2,3-dihydropyridazine-4-carbonitrile,
2-((5-(4-bromophenyl)-1,3,4-oxadiazol-2-yl)methyl)-4,5-dichloropyridazin-3(2)-one,
4,5-dichloro-2-((5-(thiophen-2-yl)-1,3,4-oxadiazol-2-yl)methyl)pyridazin-3(2)-one,
2-((5-(2-bromophenyl)-1,3,4-oxadiazol-2-yl)methyl)-4,5-dichloropyridazin-3(2H)-one.

In a particular embodiment, the compound of formula I is not 4,5-dichloro-2-((5-(4-chlorophenyl)-1,3,4-oxadiazol-2-yl)methyl)pyridazin-3-one.

In particular embodiments, where Y represents aryl optionally substituted by one or more groups independently selected from $G^{1c}$ and $G^{1c}$ represents $R^{a2}$, $R^{a2}$ does not represent —$CH_3$.

In particular embodiments (e.g. where Y represents aryl optionally substituted by one or more groups independently selected from $G^{1c}$), $G^{1c}$ represents F, $R^{a2}$ (e.g. where $R^{a2}$ does not represent —$CH_3$, e.g. $R^{a2}$ represents —$CHF_2$, —$CF_3$ or $C_{2-6}$ alkyl) —CN, -$A^{a1}$-C($Q^{a2}$)$R^{b2}$, -$A^{b1}$-C(O)N($R^{c2}$)$R^{d2}$, -$A^{c1}$-C(O)O$R^{e2}$, -$A^{d1}$-S(O)$_q$$R^{f2}$, -$A^{f1}$-S(O)$_q$N($R^{h2}$)$R^{i2}$, —N($R^{k2}$)$R^{l2}$, —O$R^{m2}$ or —S$R^{n2}$.

In more particular embodiments (e.g. where Y represents aryl optionally substituted by one or more groups independently selected from $G^{1c}$):

$G^{1c}$ represents F, $R^{a2}$, —CN, -$A^{a1}$-C($Q^{a2}$)$R^{b2}$, -$A^{b1}$-C(O)N($R^{c2}$)$R^{d2}$, -$A^{c1}$-C(O)O$R^{e2}$, -$A^{d1}$-S(O)$_q$$R^{f2}$, -$A^{f1}$-S(O)N($R^{h2}$)$R^{i2}$, —N($R^{k2}$)$R^{l2}$, —O$R^{m2}$ or —S$R^{n2}$;

$R^{a2}$ represents —$CHF_2$, —$CF_3$, $C_{2-6}$ alkyl optionally substituted by one or more groups independently selected from $G^{3a}$ or heterocycloalkyl optionally substituted by one or more groups independently selected from $G^{3b}$;

$R^{f2}$ represents $C_{1-6}$ alkyl optionally substituted by one or more groups independently selected from $G^{3a}$ or heterocycloalkyl optionally substituted by one or more groups independently selected from $G^{3b}$;

$R^{m2}$ represents H, —$CHF_2$, —$CF_3$, $C_{2-6}$ alkyl optionally substituted by one or more groups independently selected from $G^{3a}$ or heterocycloalkyl optionally substituted by one or more groups independently selected from $G^{3b}$;

each $R^{b2}$, $R^{c2}$, $R^{d2}$, $R^{e2}$, $R^{g2}$, $R^{h2}$, $R^{i2}$, $R^{j2}$, $R^{k2}$, $R^{m2}$ and $R^{n2}$ independently represents H, $C_{1-6}$ alkyl optionally substituted by one or more groups independently selected from $G^{3a}$, or heterocycloalkyl optionally substituted by one or more groups independently selected from $G^{3b}$, or any two $R^{c2}$ and $R^{d2}$, $R^{h1}$ and $R^{i1}$ and/or $R^{k1}$ and $R^{l1}$ are linked together to form, along with the nitrogen atom to which they are attached, a 3- to 6-membered ring, which ring optionally contains one further heteroatom and which ring optionally is substituted by one or more groups independently selected from halogen, $C_{1-3}$ alkyl optionally substituted by one or more halogens, and =O;
each $G^{3a}$ and $G^{3b}$ independently represents F, Cl, —CN, —N($R^{a5}$)$R^{b5}$, —O$R^{c5}$ or —S$R^{d5}$; and
each $R^{a5}$, $R^{b5}$, $R^{c5}$ and $R^{d5}$ independently represents H, methyl or ethyl.

In particular embodiments, each $R^{a1}$, $R^{f1}$, $R^{j1}$ and $R^{k1}$ independently represents $C_{1-6}$ alkyl optionally substituted by one or more groups independently selected from $G^{2a}$.

Particular compounds of the invention that may be mentioned include those in which $R^4$ represents F or $C_1$ alkyl optionally substituted by one or more F (e.g. where $R^4$ represents —$CH_3$).

More particular compounds of the invention that may be mentioned include those in which W represents —$CH_2$—.

Particular compounds of the invention that may be mentioned include those in which X represents O.

Further compounds of the invention that may be mentioned include those in which X represents S.

In particular embodiments, Y represents aryl optionally substituted by one or more groups independently selected from $G^{1c}$, or heteroaryl optionally substituted by one or more groups independently selected from $G^{1d}$.

In more particular embodiments, Y represents aryl optionally substituted by one or more groups independently selected from $G^{1c}$.

Particular compounds of formula I that may be mentioned include those in which Y represents phenyl optionally substituted by one or more (e.g. one) groups independently selected from $G^{1c}$,
more particularly where $G^1C$ represents halo, $R^{a2}$, —$NO_2$ or —$OR^{m2}$.

More particular compounds of formula I that may be mentioned include those in which: Y represents phenyl optionally substituted by one or more (e.g. one) groups independently selected from $G^{1c}$ (such as phenyl substituted with one $G^{1c}$ group in the 4-position, i.e. the para position relative to the point of attachment to the essential 5-membered ring);
$G^{1c}$ represents halo, $R^{a2}$, —$NO_2$ or —$OR^{m2}$; and
$R^{a2}$ and $R^{m2}$ represent methyl.

Particular compounds of formula I that may be mentioned include those in which $G^1C$ represents halo, such as chloro.

Thus, more particular compounds of formula I that may be mentioned include those in which:
Y represents phenyl optionally substituted by one or more (e.g. one) groups independently selected from $G^1C$ (such as phenyl substituted with one $G^{1c}$ group in the 4-position, i.e. the para position relative to the point of attachment to the essential 5-membered ring);
$G^{1c}$ represents chloro.

For example, compounds of the invention that may be mentioned include those in which Y represents para-chloro phenyl.

Particular compounds of the invention that may be mentioned include those in which Z represents O.

Particular compounds of the invention that may be mentioned include those in which:
$R^1$ represents H, halo, $R^{a1}$, —CN, —C(O)$R^{b1}$, —C(O)O$R^{e1}$, —S(O)$_2R^{f1}$ or —$NO_2$; and/or
$R^{a1}$, $R^{b1}$, $R^{e1}$ and $R^{f1}$ represents $C_{1-6}$ alkyl (e.g. methyl) optionally substituted by one or more F.

More particular compounds of the invention that may be mentioned include those in which $R^1$ represents H, halo (e.g. Cl or Br), —$CH_3$, —$CF_3$ (such as where $R^1$ represents Cl).

Particular compounds of the invention that may be mentioned include those in which $R^2$ represents H, halo (e.g. Cl or Br), —CN or —$N_3$ (such as where $R^2$ represents Cl).

More particular compounds of the invention that may be mentioned include those in which $R^2$ represents H or halo (e.g. Cl).

Thus, in particular embodiments each of $R^1$ and $R^2$ independently represents H or halo (such as Cl). In more particular embodiments, both of $R^1$ and $R^2$ represent Cl.

Particular compounds of the invention that may be mentioned include those in which $R^3$ represents H, halo (e.g. Cl or Br) or $R^{j1}$.

More particular compounds of the invention that may be mentioned include those in which $R^3$ represents H or $C_{1-6}$ alkyl optionally substituted by one or more F.

In particular embodiments, $R^3$ represents H.

In more particular embodiments:
both of $R^1$ and $R^2$ represent Cl; and
$R^3$ represents H.

Particular compounds of the invention that may be mentioned include the compounds of the examples as provided herein, or a pharmaceutically acceptable salt thereof.

Where an example compound is indicated to have been obtained in a particular salt form, the skilled person will understand that particular compounds of the invention that may be mentioned include the free base or free acid (as appropriate) of that compound, and vice versa. Further, where an example compound is indicated to have been obtained in a particular salt form, particular compounds of the invention that may be mentioned include other (i.e. different) pharmaceutically acceptable salts of that compound.

Thus, for the avoidance of doubt, particular compounds of the invention that may be mentioned include:
4,5-dichloro-2-((5-(4-chlorophenyl)-1,3,4-oxadiazol-2-yl)methyl)pyridazin-3-one,
and pharmaceutically acceptable salts thereof.

Compositions and Medical Uses

As discussed hereinbefore, compounds of the invention, and therefore compositions and kits comprising the same, are useful as pharmaceuticals.

According to a second aspect of the invention there is provided a compound of the invention, as hereinbefore defined (i.e. in the first aspect of the invention, including all embodiments and particular features therein), for use as a pharmaceutical. Further, there is provided a compound of the invention, as hereinbefore defined, for use in medicine.

For the avoidance of doubt, in a particular embodiment of the second aspect of the invention, the compound of formula I is not a compound selected from the list provided in proviso (A) herein.

As indicated herein, compounds of the invention may be of particular use in treating cancers.

Thus, in a third aspect of the invention, there is provided a compound of the invention, as hereinbefore defined (i.e. in the first aspect of the invention, including all embodiments and particular features therein), for use in the treatment of cancer.

In an alternative third aspect of the invention, there is provided the use of a compound of the invention, as hereinbefore defined, in the manufacture of a medicament for the treatment of cancer.

In a further alternative third aspect of the invention, there is provided a method of treating cancer comprising administering to a patient in need thereof a therapeutically effective amount of a compound of the invention.

For the avoidance of doubt, in a particular embodiment of the third aspect of the invention, the compound of formula I is not 4,5-dichloro-2-((5-(4-chlorophenyl)-1,3,4-oxadiazol-2-yl)methyl)pyridazin-3-one.

The skilled person will understand that references to the treatment of a particular condition (or, similarly, to treating that condition) take their normal meanings in the field of medicine. In particular, the terms may refer to achieving a reduction in the severity of one or more clinical symptom associated with the condition. For example, in the case of a cancer, the term may refer to achieving a reduction of the amount of cancerous cells present (e.g. in the case of a cancer forming a solid tumour, indicated by a reduction in tumour volume).

As used herein, references to patients will refer to a living subject being treated, including mammalian (e.g. human) patients.

As used herein, the term effective amount will refers to an amount of a compound that confers a therapeutic effect on the treated patient. The effect may be objective (i.e. measurable by some test or marker) or subjective (i.e. the subject gives an indication of or feels an effect).

Although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the active compounds to which they are metabolised) may therefore be described as "prodrugs" of compounds of the invention.

As used herein, references to prodrugs will include compounds that form a compound of the invention, in an experimentally-detectable amount, within a predetermined time, following enteral or parenteral administration (e.g. oral or parenteral administration). All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the active compounds of the invention to which they are metabolised), may also be described as "prodrugs".

Thus, the compounds of the invention are useful because they possess pharmacological activity, and/or are metabolised in the body following oral or parenteral administration to form compounds that possess pharmacological activity.

As indicated herein, the compounds of the invention may be useful in the treatment of cancer (i.e. particular cancers).

Particular cancers that may be mentioned include those selected from the group comprising:

soft tissue cancers, such as sarcoma (e.g. angiosarcoma, fibrosarcoma, rhabdomyosarcoma, liposarcoma), myxoma, rhabdomyoma, fibroma, lipoma and teratoma;

lung cancers, such as bronchogenic carcinoma (e.g. squamous cell, undifferentiated small cell, undifferentiated large cell, adenocarcinoma), alveolar (or bronchiolar) carcinoma, bronchial adenoma, sarcoma, lymphoma, chondromatous hamartoma, mesothelioma;

gastrointestinal cancers: such as esophageal cancers (e.g. squamous cell carcinoma, adenocarcinoma, leiomyosarcoma, lymphoma), stomach cancers (e.g. carcinoma, lymphoma, leiomyosarcoma), pancreatic cancers (e.g. ductal adenocarcinoma, insulinoma, glucagonoma, gastrinoma, carcinoid tumors, vipoma), small bowel cancers (e.g. adenocarcinoma, lymphoma, carcinoid tumors, Kaposi's sarcoma, leiomyoma, hemangioma, lipoma, neurofibroma, fibroma), large bowel cancers (e.g. adenocarcinoma, tubular adenoma, villous adenoma, hamartoma, leiomyoma);

genitourinary tract cancers, such as cancer of the kidney (e.g. adenocarcinoma, Wilm's tumor (nephroblastoma), lymphoma, leukemia), bladder and urethra (e.g. squamous cell carcinoma, transitional cell carcinoma, adenocarcinoma), prostate (e.g. adenocarcinoma, sarcoma), testis (e.g. seminoma, teratoma, embryonal carcinoma, teratocarcinoma, choriocarcinoma, sarcoma, interstitial cell carcinoma, fibroma, fibroadenoma, adenomatoid tumors, lipoma);

liver cancers, such as hepatoma (e.g. hepatocellular carcinoma), cholangiocarcinoma, hepatoblastoma, angiosarcoma, hepatocellular adenoma, hemangioma;

bone cancers, such as osteogenic sarcoma (e.g. osteosarcoma), fibrosarcoma, malignant fibrous histiocytoma, chondrosarcoma, Ewing's sarcoma, malignant lymphoma (e.g. reticulum cell sarcoma), multiple myeloma, malignant giant cell tumor chordoma, osteochronfroma (e.g osteocartilaginous exostoses), benign chondroma, chondroblastoma, chondromyxofibroma, osteoid osteoma and giant cell tumors;

cancers of the head and/or nervous system, such as cancer of the skull (e.g. osteoma, hemangioma, granuloma, xanthoma, osteitis deformans), meninges (e.g. meningioma, meningiosarcoma, gliomatosis), brain (e.g. astrocytoma, medulloblastoma, glioma, ependymoma, germinoma (pinealoma), glioblastoma multiform, oligodendroglioma, schwannoma, retinoblastoma, congenital tumors), spinal cord (e.g. neurofibroma, meningioma, glioma, sarcoma);

gynecological cancers, such as cancers of the uterus (e.g. endometrial carcinoma), cervix (cervical carcinoma, pretumor cervical dysplasia), ovaries (e.g. ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), cancers of the vulva (e.g. squamous cell carcinoma, intraepithelial carcinoma, adenocarcinoma, fibrosarcoma, melanoma), vagina (e.g. clear cell carcinoma, squamous cell carcinoma, botryoid sarcoma (embryonal rhabdomyosarcoma)), fallopian tubes (e.g. carcinoma);

haematologic cancers, such as cancers of the blood and bone marrow (e.g. myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma);

skin cancers, such as malignant melanoma, basal cell carcinoma, squamous cell carcinoma, Kaposi's sarcoma, moles dysplastic nevi, lipoma, angioma, dermatofibroma, keloids;

neurofibromatosis and Adrenal glands; and neuroblastomas.

As used herein, references to cancerous cells and the like will include references to a cell afflicted by any one of the above identified conditions.

More particular cancers that may be mentioned include those corresponding to the cell lines used in the examples provided herein.

For example, more particular cancers that may be mentioned include:
head and neck cancer (such as throat cancer, e.g. pharyngeal squamous cell carcinoma);
colon cancer (such as colorectal carcinoma);
skin cancer (such as epidermoid (skin) carcinoma);
gastrointestinal cancers (such as pancreatic cancer, e.g. pancreatic ductal carcinoma); breast cancer (such as mammary adenocarcinoma, e.g. metastatic mammary adenocarcinoma);
lung cancer (such as carcinoma); and
haematologic cancers (such as leukemia, e.g. acute monocytic leukemia).

In particular embodiments, the cancer is a solid tumor cancer.

In more particular embodiments, the cancer is selected from pancreatic cancer, ovarian cancer and colorectal cancer.

For example, in certain embodiments, the cancer is selected from colorectal cancer (including those processing Ras mutations), small cell lung cancer, non-small cell lung cancer (NSCLC), and glioma.

In other embodiments, the cancer is selected from non-small cell lung cancer, ovarian cancer, metastatic breast cancer, pancreatic cancer, hepatobiliary cancer (including hepatocellular cancer, bile duct cancer and cholangiocarcinoma), and gastric cancer.

In further embodiments, the cancer is selected from colorectal cancer (including Ras mutations), small cell lung cancer, non-small cell lung cancer, ovarian cancer, hepatobiliary cancer (including hepatocellular cancer, bile duct cancer and cholangiocarcinoma), gastric cancer, testicular cancer, and head and neck squamous cell carcinoma.

In certain embodiments of the present invention, the cancer is selected from leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostate cancer The skilled person will understand that treatment with compounds of the invention may further comprise (i.e. be combined with) further treatment(s) for the same condition. In particular, treatment with compounds of the invention may be combined with means for the treatment of cancer, such as treatment with one or more other therapeutic agent that is useful in the in the treatment of cancer and/or one or more physical method used in the treatment of cancer (such as treatment through surgery), as known to those skilled in the art.

In particular, treatment with compounds of the invention may be performed in patients who are being or have been (i.e. as part or of a treatment for the same condition, such as within a month of treatment with compounds of the invention, such as within two weeks, e.g. within a week or, particularly, on the same day) treated with a therapeutic agent or physical method that is capable of causing (e.g. can be demonstrated to cause) an increase in reactive oxygen species.

For the avoidance of doubt, the skilled person will understand that therapeutic agents or physical methods capable of causing (e.g. can be demonstrated to cause) an increase in reactive oxygen species may not necessarily be effective treatments per se, but will become effective when used in combination with compounds of the invention.

For the avoidance of doubt, the skilled person will understand that compounds of the invention may also be used in combination with one or more other therapeutic agent that is useful in the in the treatment of cancer and/or one or more physical method used in the treatment of cancer (such as treatment through surgery) wherein such methods do not cause an increase in reactive oxygen species.

Thus, there is also provided:
a method of treating cancer in a patient in need thereof wherein the patient is administered a therapeutically effective amount of a compound of the invention in combination with treatment by radiotherapy (i.e. concomitantly or sequentially); and
a compound of the invention for use in treating cancer in a patient who is also being treated with radiotherapy.

Compounds of the invention will normally be administered orally, intravenously, subcutaneously, buccally, rectally, dermally, nasally, tracheally, bronchially, sublingually, intranasally, topically, by any other parenteral route or via inhalation, in a pharmaceutically acceptable dosage form.

Compounds of the invention may be administered alone or may be administered by way of known pharmaceutical compositions/formulations, including tablets, capsules or elixirs for oral administration, suppositories for rectal administration, sterile solutions or suspensions for parenteral or intramuscular administration, and the like.

According to a fourth aspect of the invention there is thus provided a pharmaceutical composition/formulation comprising a compound of the invention, as hereinbefore defined (i.e. in the first aspect of the invention), and optionally (e.g. in admixture with) one or more pharmaceutically acceptable adjuvant, diluent and/or carrier.

For the avoidance of doubt, in a particular embodiment of the fourth aspect of the invention, the compound of formula I is not a compound selected from the list provided in proviso (A) herein.

The skilled person will understand that references herein to compounds of the invention being for particular uses (and, similarly, to uses and methods of use relating to compounds of the invention) may also apply to pharmaceutical compositions comprising compounds of the invention as described herein.

Compounds of the invention may be administered in the form of tablets or capsules, e.g. time-release capsules that are taken orally. Alternatively, the compounds of the invention may be in a liquid form and may be taken orally or by injection. The compounds of the invention may also be in the form of suppositories, or, creams, gels, and foams e.g. that can be applied to the skin. In addition, they may be in the form of an inhalant that is applied nasally or via the lungs.

The skilled person will understand that compounds of the invention may act systemically and/or locally (i.e. at a particular site).

Compounds of the invention may be administered orally, intravenously, subcutaneously, buccally, rectally, dermally, nasally, tracheally, bronchially, by any other parenteral route or via inhalation, in a pharmaceutically acceptable dosage form. Alternatively, particularly where compounds of the invention are intended to act locally, compounds of the invention may be administered topically.

Thus, in a particular embodiment, the pharmaceutical formulation is provided in a pharmaceutically acceptable dosage form, including tablets or capsules, liquid forms to be taken orally or by injection, suppositories, creams, gels, foams, or inhalants (e.g. to be applied intranasally). For the avoidance of doubt, in such embodiments, compounds of the invention may be present as a solid (e.g. a solid dispersion), liquid (e.g. in solution) or in other forms, such as in the form of micelles.

In a more particular embodiments, the pharmaceutical formulation is provided the form of a tablets or capsules, liquid forms to be taken orally or by injection (e.g. a form suitable for intravenous injection). In particular, injection may take place using conventional means, and may include the use of microneedles.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

As described herein, compounds of the invention may also be combined with one or more other (i.e. different, e.g. agents other than compounds of formula I) therapeutic agents that are useful in the treatment of cancer. Such combination products that provide for the administration of a compound of the invention in conjunction with one or more other therapeutic agent may be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the one or more other therapeutic agent).

Thus, according to a fifth aspect of the invention, there is provided a combination product comprising:
(I) a compound of the invention, as hereinbefore defined (i.e. in the first aspect of the invention); and
(II) one or more other therapeutic agent that is useful in the treatment of cancer,
wherein each of components (I) and (II) is formulated in admixture, optionally with one or more a pharmaceutically-acceptable adjuvant, diluent or carrier.

In a sixth aspect of the invention there is provided a kit-of-parts comprising:
(a) a pharmaceutical formulation as hereinbefore defined (i.e. in the; and
(b) one or more other therapeutic agent that is useful in the treatment of cancer, optionally in admixture with one or more pharmaceutically-acceptable adjuvant, diluent or carrier,
which components (a) and (b) are each provided in a form that is suitable for administration in conjunction (i.e. concomitantly or sequentially) with the other.

For the avoidance of doubt, in a particular embodiment of the third aspect of the invention, the compound of formula I is not 4,5-dichloro-2-((5-(4-chlorophenyl)-1,3,4-oxadiazol-2-yl)methyl)pyridazin-3-one.

Compounds of the invention may be administered at varying doses. Oral, pulmonary and topical dosages (and subcutaneous dosages, although these dosages may be relatively lower) may range from between about 0.01 mg/kg of body weight per day (mg/kg/day) to about 100 mg/kg/day, preferably about 0.01 to about 10 mg/kg/day, and more preferably about 0.1 to about 5.0 mg/kg/day. For e.g. oral administration, the compositions typically contain between about 0.01 mg to about 2000 mg, for example between about 0.1 mg to about 500 mg, or between 1 mg to about 100 mg, of the active ingredient. Intravenously, the most preferred doses will range from about 0.001 to about 10 mg/kg/hour during constant rate infusion. Advantageously, compounds may be administered in a single daily dose, or the total daily dosage may be administered in divided doses of two, three or four times daily.

In any event, the physician, or the skilled person, will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

Preparation of Compounds/Compositions

Pharmaceutical compositions/formulations, combination products and kits as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically-acceptable adjuvant, diluent or carrier.

In further aspects of the invention, there is provided a process for the preparation of a combination product or kit-of-parts as hereinbefore defined, which process comprises bringing into association a compound of the invention, as hereinbefore defined, or a pharmaceutically acceptable salt thereof with the other therapeutic agent that is useful in the treatment of cancer, and at least one pharmaceutically-acceptable adjuvant, diluent or carrier.

As used herein, references to bringing into association will mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Compounds of the invention as described herein may be prepared in accordance with techniques that are well known to those skilled in the art, such as those described in the examples provided hereinafter.

According to a seventh aspect of the invention there is provided a process for the preparation of a compound of the invention as hereinbefore defined, which process comprises:
(i) reaction of a compound of formula II

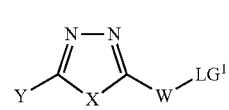

(II)

wherein W, X and Y are as defined herein in formula I (or any particular feature or embodiments thereof) and LG¹ represents a suitable leaving group (such as a halo, e.g. Cl), with a compound of formula III

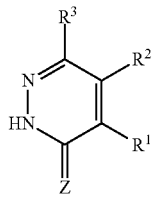 (III)

wherein $R^1$ to $R^3$ and Z are as defined herein in formula I (or any particular feature or embodiments thereof), in the presence of a suitable base (such as a metal carbonate, e.g. sodium carbonate) and in the presence of a suitable solvent (such as a polar organic solvent, e.g. N,N-dimethylformamide); or (ii) reaction of a compound of formula IV

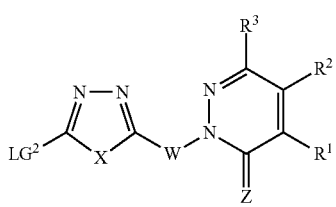 (IV)

wherein W, X, Z and $R^1$ to $R^3$ are as defined herein in formula I (or any particular feature or embodiments thereof) and $LG^2$ represents a suitable leaving group (such as a halo, e.g. Cl), with a compound of formula V

Y—$B^1$ (V)

wherein Y is as defined herein in formula I (or any particular feature or embodiments thereof) and $B^1$ represents a group suitable for participating in a coupling (e.g. a Pd-catalysed coupling) reaction (such as a boronic acid, e.g. forming a —B(OH)$_2$ group) in the presence of (e.g. in the presence of a catalytic amount of) a suitable catalyst (such as a Pd catalyst, for example a Pd(O) catalyst, e.g. tetrakis(triphenylphosphine)palladium(0)) and in the presence of a suitable solvent (such as a polar organic solvent, e.g. tetrahydrofuran).

Compounds of formulae II, III, IV and V are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "*Comprehensive Organic Synthesis*" by B. M. Trost and I. Fleming, Pergamon Press, 1991. Further references that may be employed include "*Heterocyclic Chemistry*" by J. A. Joule, K. Mills and G. F. Smith, 3$^{rd}$ edition, published by Chapman & Hall, "*Comprehensive Heterocyclic Chemistry II*" by A. R. Katritzky, C. W. Rees and E. F. V. Scriven, Pergamon Press, 1996 and "*Science of Synthesis*", Volumes 9-17 (Hetarenes and Related Ring Systems), Georg Thieme Verlag, 2006.

For example, compounds of formula II where X represents O may be prepared by reaction of a compound of formula VI

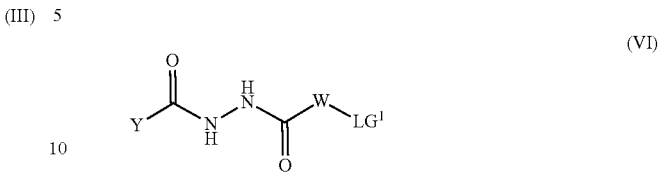 (VI)

wherein W, and Y are as defined herein in formula I (or any particular feature or embodiments thereof) and $LG^1$ is as defined herein in formula II in the presence of a reagent suitable for performing the ring closure, such as phosphoryl chloride (POCl$_3$; e.g. in neat POCS$_3$) and in the presence of a suitable solvent (such as a polar organic solvent, e.g. N,N-dimethylformamide or tetrahydrofuran), under conditions known to those skilled in the art.

Similarly, compounds of formula II where X represents S may be prepared by reaction of a compound of formula VI as defined herein in the presence of phosphorous pentasulphide or Lawesson's reagent, under conditions known to those skilled in the art.

Further, compounds of formula III where Z represents O and $R^3$ represents H may be prepared by reaction of compounds of formula VII

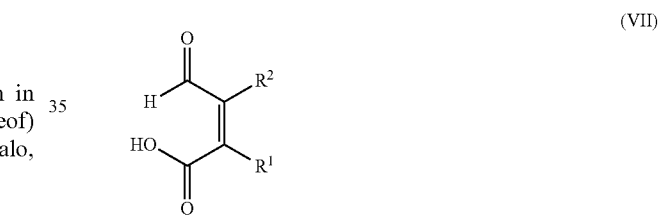 (VII)

wherein $R^1$ and $R^2$ are as defined herein in formula I (or any particular feature or embodiments thereof), with hydrazine or a salt thereof (e.g. hydrazine sulphate or hydrazine chloride), under conditions known to those skilled in the art.

Similarly, compounds of formulae VII and VIII are either commercially available, are known in the literature, or may be obtained either by analogy with the processes described herein, or by conventional synthetic procedures, in accordance with standard techniques, from available starting materials using appropriate reagents and reaction conditions.

The substituents $R^1$ to $R^3$, W, X, Y, Z, $B^1$, $LG^1$ and $LG^2$ as hereinbefore defined, may be modified one or more times, after or during the processes described above for preparation of compounds of formula I by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. The precursor groups can be changed to a different such group, or to the groups defined in formula I, at any time during the reaction sequence. The skilled person may also refer to "*Comprehensive Organic Functional Group Transformations*" by A. R. Katritzky, O. Meth-Cohn and C. W. Rees, Pergamon Press, 1995 and/or "*Comprehensive Organic Transformations*" by R. C. Larock, Wiley-VCH, 1999.

Compounds of the invention may be isolated from their reaction mixtures and, if necessary, purified using conventional techniques as known to those skilled in the art. Thus, processes for preparation of compounds of the invention as described herein may include, as a final step, isolation and optionally purification of the compound of the invention (e.g. isolation and optionally purification of the compound of formula I).

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be applied and removed in accordance with techniques that are well known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "*Protective Groups in Organic Synthesis*", 3rd edition, T. W. Greene & P. G. M. Wutz, Wiley-Interscience (1999).

Compounds of the invention may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, compounds of the invention may have the advantage that they are more efficacious and/or exhibit advantageous properties in vivo.

Without wishing to be bound by theory, it is thought that inhibition of thioredoxin reductase is obtained by the utilization of strong electrophilicity of small molecule inhibitors in combination with a pronounced inherent nucleophilicity of NADPH-reduced, but not oxidized, thioredoxin reductase, resulting in selective and potent inhibition of said enzyme without major targeting of other cellular pathways or enzymes.

Moreover, it is thought that normal non-cancerous cells may survive without a functional cytosolic thioredoxin reductase enzyme because of maintained function of the glutathione system, while cancer cells cannot survive upon specific inhibition of cytosolic thioredoxin reductase.

EXAMPLES

The invention is illustrated by way of the following examples, in which the following abbreviations may be employed.

aq aqueous
BSA bovine serum albumin
DMA N,N-dimethylacetamide
DMSO dimethyl sulphoxide
DTNB 5,5'-dithio-bis-(2-nitrobenzoic acid)
EDTA ethylenediaminetetraacetic acid
GSSG gluthathione disulfide
HPLC high performance liquid chromatography
HRMS high resolution mass spectrometry
NADPH nicotinamide adenine dinucleotide phosphate
NMR nuclear magnetic resonance
PBS phosphate buffered saline
rt room temperature Starting materials and chemical reagents specified in the syntheses described below are commercially available from a number of suppliers, such as Sigma Aldrich.

In the event that there is a discrepancy between nomenclature and the structure of compounds as depicted graphically, it is the latter that presides (unless contradicted by any experimental details that may be given and/or unless it is clear from the context).

Final compounds are named using ChemBioDraw Ultra 14.

Example 1: 4,5-dichloro-2-((5-(4-chlorophenyl)-1,3,4-oxadiazol-2-yl)methyl)pyridazin-3-one

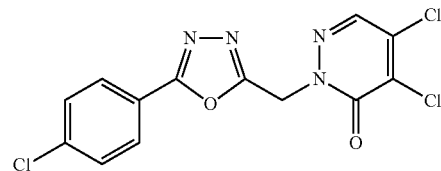 [SMILES: O=c1c(Cl)c(Cl)cnn1Cc1nnc(-c2ccc(Cl)cc2)o1]

The compound of Example 1 was obtained commercially and its identity confirmed by HRMS.

BIOLOGICAL EXAMPLES

Biological Example 1: Inhibition of Recombinant TrxR1 and GR

Small molecule inhibition of recombinant thioredoxin reductase 1 (TrxR1) and gluthathione reductase (GR) was examined in 96-well plate format. 15 nM TrxR1 was incubated in the presence of 250 μM NADPH, 0.1 mg/ml BSA, and various concentrations of the compound of Example 1 (1% DMSO final) in 50 mM Tris (pH 7.5) and 2 mM EDTA buffer for 15 minutes. Following the incubation period, 2.5 mM DTNB was added to each well and the change in O.D. at 412 nm was followed. Percent activity was determined using DMSO vehicle and no TrxR1 (blank) controls. 2 nM GR was incubated in the presence of 250 μM NADPH, 0.1 mg/ml BSA, and various concentrations of compounds (1% DMSO final) in 50 mM Tris (pH 7.5) and 2 mM EDTA buffer for 15 minutes. Following the incubation period, 1 mM GSSG was added to each well and the change in O.D. at 340 nm was followed. Percent activity was determined using DMSO vehicle and no GR (blank) controls.

Figure 1:
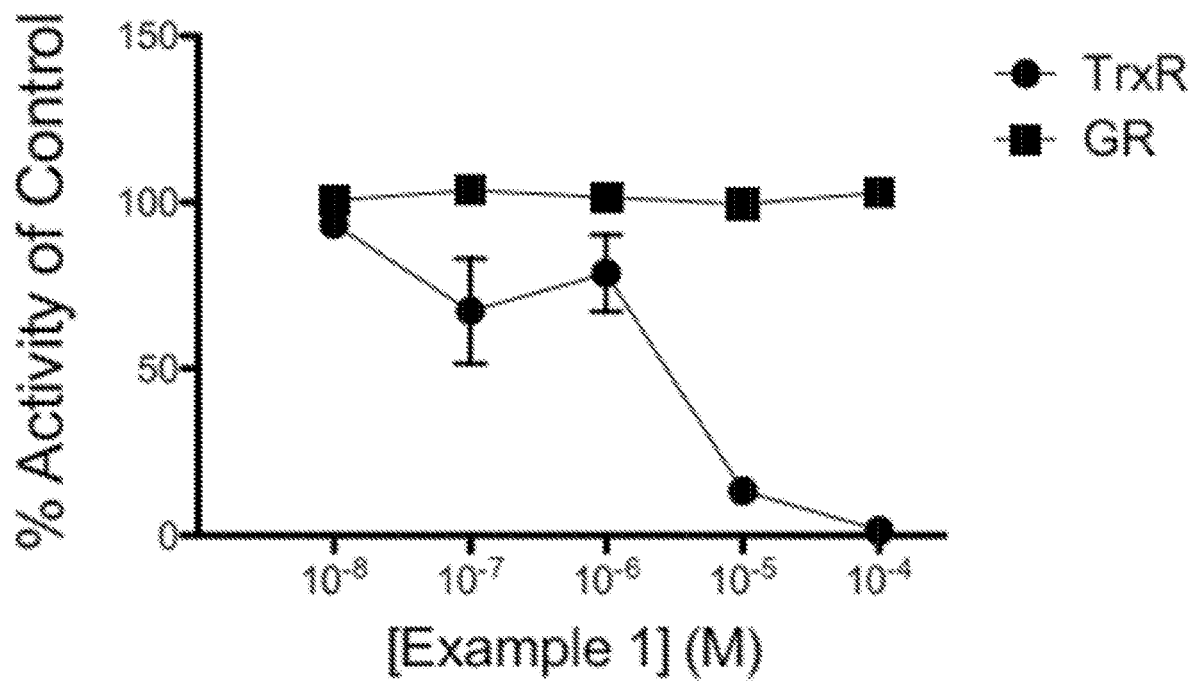
FIG. 1 shows results obtained from the experiment described in Biological Example 1 for the compound of Example 1.

Using the assays described in Biological Example 1, the following IC$_{50}$ values were obtained. Results obtained for the compound of Example 1 are also represented in FIG. 1.

| Example | TrxR inhibition (μM) | GR inhibition (μM) |
|---|---|---|
| 1 | 1.85 | >100 |

Biological Example 2: Cell Culture

Cell lines were plated 2000 cells/well in 96-well black optical plates in the presence of 10% FBS media containing 25 nM selenite. The following day cells were treated with various concentrations of the compound of Example 1 (0.1% DMSO final) and incubated for 72 hrs. After the incubation Cell-Quanti Blue reagent was added to each well and incubated for additional 3 hrs. Fluorescence was read ex: 530 nm/em: 590 nm, and percent of viability was determined using DMSO vehicle and no cell (blank) controls.

Figure 2:
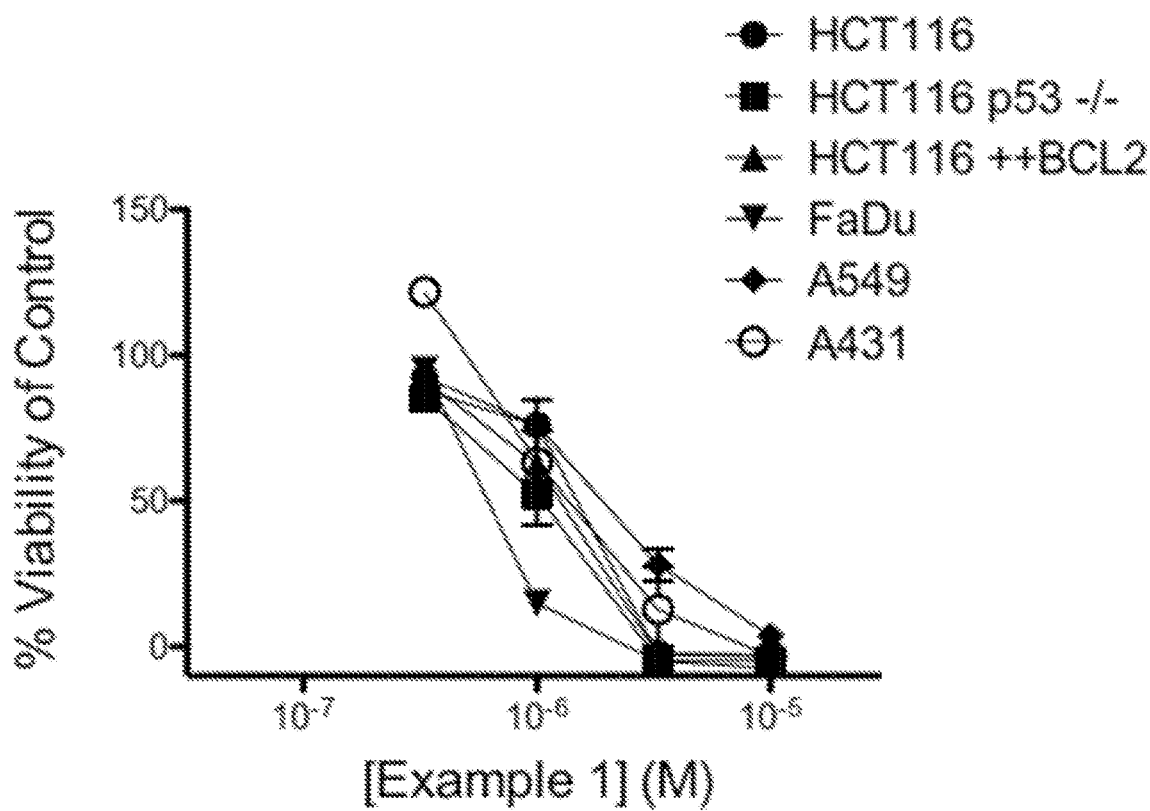
FIG. 2 shows results obtained from the experiment described in Biological Example 2 (using the compound of Example 1).

Various results obtained are provided in FIG. 2 herein, wherein data for the following cell lines is presented.

| Cell line | Cell type |
|---|---|
| FaDu | pharyngeal squamous cell carcinoma |
| HCT116 | colorectal carcinoma |
| HCT116 p53 | colorectal carcinoma |
| HCT116 ++ BLC2 | colorectal carcinoma |
| A431 | epidermoid (skin) carcinoma |
| A549 | lung carcinoma |

The invention claimed is:
1. A compound of formula I

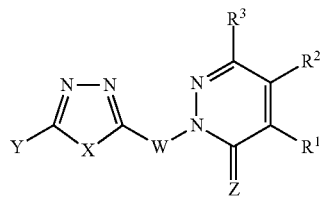

(I)

or a pharmaceutically acceptable salt thereof, wherein:
W represents C$_1$ alkylene optionally substituted by one or more groups independently selected from R$^4$;
X represents O;
Y represents C$_{1-6}$ alkyl optionally substituted by one or more groups independently selected from G$^{1a}$, C$_{2-6}$ alkenyl optionally substituted by one or more groups independently selected from G$^{1a}$, C$_{2-6}$ alkynyl optionally substituted by one or more groups independently selected from G$^{1a}$, heterocycloalkyl optionally substituted by one or more groups independently selected from G$^{1b}$, aryl optionally substituted by one or more groups independently selected from G$^{1c}$, or heteroaryl optionally substituted by one or more groups independently selected from G$^{1d}$;
Z represents O, S or NR$^5$;
R$^1$ represents H, halo, R$^{a1}$, —CN, —C(Q$^{a1}$)R$^{b1}$, —C(Q$^{b1}$)N(R$^{c1}$)R$^{d1}$, —C(Q$^{c1}$)OR$^{e1}$, —S(O)$_n$R$^{f1}$, —S(O)$_p$N(R$^{g1}$)R$^{h1}$, —S(O)$_p$OR$^{i1}$ or —NO$_2$;
R$^2$ represents H, halo, —CN or —N$_3$;
R$^3$ represents H, halo or R$^{dj1}$;
R$^4$ represents halo, C$_{1-6}$ alkyl optionally substituted by one or more groups independently selected from G$^{1e}$, C$_{2-6}$ alkenyl optionally substituted by one or more groups independently selected from G$^{1e}$, or C$_{2-6}$ alkynyl optionally substituted by one or more groups independently selected from G$^{1e}$;
R$^5$ represents H, R$^{k1}$, —OR$^{1l}$ or —N(R$^{m1}$)R$^{n1}$,
Q$^{a1}$ to Q$^{c1}$ each independently represents =O, =S, =NR$^{o1}$ or =N(OR$^{p1}$);
each R$^{a1}$, R$^{f1}$, R$^{j1}$ and R$^{k1}$ independently represents C$_{1-6}$ alkyl optionally substituted by one or more groups independently selected from G$^{2a}$, C$_{2-6}$ alkenyl optionally substituted by one or more groups independently selected from G$^{2a}$, C$_{2-6}$ alkynyl optionally substituted by one or more groups independently selected from G$^{2a}$, or heterocycloalkyl optionally substituted by one or more groups independently selected from G$^{2b}$;
each R$^{b1}$, R$^{c1}$, R$^{d1}$, R$^{e1}$, R$^{g1}$, R$^{h1}$, R$^{i1}$, R$^{j1}$, R$^{l1}$, R$^{m1}$, R$^{o1}$ and R$^{p1}$ independently represents H, C$_{1-6}$ alkyl optionally substituted by one or more groups independently selected from G$^{2a}$, C$_{2-6}$ alkenyl optionally substituted by one or more groups independently selected from G$^{2a}$, C$_{2-6}$ alkynyl optionally substituted by one or more groups independently selected from G$^{2a}$, or heterocycloalkyl optionally substituted by one or more groups independently selected from G$^{2b}$,
or any two R$^{c1}$ and R$^{d1}$, R$^{g1}$ and R$^{h1}$ and/or R$^{m1}$ and R$^{n1}$ are linked together to form, along with the nitrogen atom to which they are attached, a 3- to 6-membered ring, which ring optionally contains one further heteroatom and which ring optionally is substituted by one or more groups independently selected from halogen, C$_{1-3}$ alkyl optionally substituted by one or more halogens, C$_{2-3}$ alkenyl optionally substituted by one or more halogens, C$_{2-3}$ alkynyl optionally substituted by one or more halogens, and =O;
each G$^{1a}$, G$^{1b}$, G$^{1c}$ and G$^{1d}$ represent halogen, R$^{a2}$, —CN, -A$^{a1}$-C(Q$^{a2}$)R$^{a2}$, -A$^{b1}$-C(Q$^{b2}$)N(R$^{c2}$)R$^{d2}$, -A$^{c1}$-C(Q$^{c2}$)OR$^{e2}$, -A$^{d1}$-S(O)R$^{f2}$, -A$^{e1}$-S(O)$_q$C(O)R$^{g2}$, -A$^{f1}$-S(O)$_q$N(R$^{h2}$)R$^{i2}$, -A$^{g1}$-S(O)$_q$OR$^{j2}$, —N$_3$, —N(R$^{k2}$)R$^{l2}$, —N(H)CN, —NO$_2$, —OR$^{m2}$, —SR$^{n2}$ or =Q$^{d2}$,
A$^{a1}$ to A$^{g1}$ each independently represents a single bond, —N(R$^6$)—, —C(Q$^{e2}$)N(R$^7$)— or —O—;
Q$^{a2}$ to Q$^{e2}$ each independently represents =O, =S, =NR$^{o2}$ or =N(OR$^{p2}$);
each R$^6$ and R$^7$ independently represents H, C$_{1-6}$ alkyl optionally substituted by one or more F, C$_{2-6}$ alkenyl optionally substituted by one or more F, or C$_{2-6}$ alkynyl optionally substituted by one or more F;
each R$^{a2}$ and R$^{f2}$ independently represents C$_{1-6}$ alkyl optionally substituted by one or more groups independently selected from G$^{3a}$, C$_{2-6}$ alkenyl optionally substituted by one or more groups independently selected from G$^{3a}$, C$_{2-6}$ alkynyl optionally substituted by one or more groups independently selected from G$^{3a}$, or heterocycloalkyl optionally substituted by one or more groups independently selected from G$^{3b}$;
each R$^{b2}$, R$^{c2}$, R$^{d2}$, R$^{e2}$, R$^{g2}$, R$^{h2}$, R$^{i2}$, R$^{j2}$, R$^{k2}$, R$^{l2}$, R$^{m2}$, R$^{n2}$, R$^{o2}$ and R$^{p2}$ independently represents H, C$_{1-6}$ alkyl optionally substituted by one or more groups independently selected from G$^{3a}$, C$_{2-6}$ alkenyl optionally substituted by one or more groups independently selected from G$^{3a}$, C$_{2-6}$ alkynyl optionally substituted by one or more groups independently selected from G$^{3a}$, or heterocycloalkyl optionally substituted by one or more groups independently selected from $G^{3b}$; or any two $R^{c2}$ and $R^{d2}$, $R^{h2}$ and $R^{i2}$ and/or $R^{k2}$ and $R^{l2}$ are linked together to form, along with the nitrogen atom to which they are attached, a 3- to 6-membered ring, which ring optionally contains one further heteroatom and which ring optionally is substituted by one or more groups independently selected from halogen, $C_{1-3}$ alkyl optionally substituted by one or more halogens, $C_{2-3}$ alkenyl optionally substituted by one or more halogens, $C_{2-3}$ alkynyl optionally substituted by one or more halogens, and =O;

each $G^{1e}$ independently represents halo, $R^{2a}$, —CN, —N($R^{a3}$)$R^{b3}$, —O$R^{c3}$ or —S$R^{d3}$;

$R^{a3}$, $R^{b3}$, $R^{c3}$ and $R^{d3}$ each independently represents H, $C_{1-6}$ alkyl optionally substituted by one or more F, $C_{2-6}$ alkenyl optionally substituted by one or more F, or $C_{2-6}$ alkynyl optionally substituted by one or more F;

or $R^{a3}$ and $R^{b3}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, $C_{2-3}$ alkenyl optionally substituted by one or more fluoro, $C_{2-3}$ alkynyl optionally substituted by one or more fluoro, and =O;

each $G^{2a}$ and $G^{2b}$ independently represents halo, —CN, —N($R^{a4}$)$R^{b4}$, —O$R^{c4}$, —S$R^{d4}$ or =O;

each $R^{a4}$, $R^{b4}$, $R^{c4}$ and $R^{d4}$ independently represents H, $C_{1-6}$ alkyl optionally substituted by one or more fluoro, $C_{2-6}$ alkenyl optionally substituted by one or more fluoro, or $C_{2-6}$ alkynyl optionally substituted by one or more fluoro;

or $R^{a4}$ and $R^{b4}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, $C_{2-3}$ alkenyl optionally substituted by one or more fluoro, $C_{2-3}$ alkynyl optionally substituted by one or more fluoro, and =O;

each $G^{3a}$ and $G^{3b}$ independently represents halo, —CN, —N($R^{a5}$)$R^{b5}$, —O$R^{c5}$, —S$R^{d5}$ or =O;

each $R^{a5}$, $R^{b5}$, $R^{c5}$ and $R^{d5}$ independently represents H, $C_{1-6}$ alkyl optionally substituted by one or more fluoro, $C_{2-6}$ alkenyl optionally substituted by one or more fluoro, or $C_{2-6}$ alkynyl optionally substituted by one or more fluoro;

or $R^{a5}$ and $R^{b5}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, $C_{2-3}$ alkenyl optionally substituted by one or more fluoro, $C_{2-3}$ alkynyl optionally substituted by one or more fluoro, and =O;

each n independently represents 0, 1 or 2,
each p independently represents 1 or 2,
each q independently represents 1 or 2, with the provisos that:
(A) the compound of formula I is not a compound selected from
4,5-dichloro-2-((5-(4-chlorophenyl)-1,3,4-oxadiazol-2-yl)methyl)pyridazin-3(2H)-one,
4,5-dichloro-2-((5-phenyl-1,3,4-oxadiazol-2-yl)methyl)pyridazin-3(2H)-one,
4,5-dichloro-2-((5-(p-tolyl)-1,3,4-oxadiazol-2-yl)methyl)pyridazin-3(2H)-one,
4,5-dichloro-2-(1-(5-(4-chlorophenyl)-1,3,4-oxadiazol-2-yl)propyl)pyridazin-3(2H)-one,
4,5-dichloro-2-(1-(5-phenyl-1,3,4-oxadiazol-2-yl)propyl)pyridazin-3(2H)-one,
4,5-dichloro-2-(1-(5-(p-tolyl)-1,3,4-oxadiazol-2-yl)propyl)pyridazin-3(2H)-one, and
4,5-dichloro-2-(1-(5-(4-methoxyphenyl)-1,3,4-oxadiazol-2-yl)propyl)pyridazin-3(2H)-one;
and
(B) the compound of formula I is not a compound selected from
2-((5-(thiophen-2-yl)-1,3,4-oxadiazol-2-yl)methyl)-6-(trifluoromethyl)pyridazin-3(2H)-one,
4,5-dibromo-2-((5-methyl-1,3,4-oxadiazol-2-yl)methyl)pyridazin-3(2H)-one,
5-iodo-2-((5-methyl-1,3,4-oxadiazol-2-yl)methyl)pyridazin-3(2H)-one,
2-((5-ethyl-1,3,4-oxadiazol-2-yl)methyl)-5-iodopyridazin-3(2H)-one,
4,5-dichloro-2-((5-ethyl-1,3,4-oxadiazol-2-yl)methyl)pyridazin-3(2H)-one,
4,5-dibromo-2-((5-ethyl-1,3,4-oxadiazol-2-yl)methyl)pyridazin-3(2H)-one,
4,5-dichloro-2-((5-methyl-1,3,4-oxadiazol-2-yl)methyl)pyridazin-3(2H)-one,
2-((5-(tert-butyl)-1,3,4-oxadiazol-2-yl)methyl)-4,5-dichloropyridazin-3(2H)-one,
2-((5-isopropyl-1,3,4-oxadiazol-2-yl)methyl)-6-(trifluoromethyl)pyridazin-3(2H)-one,
6-(tert-butyl)-2-((5-(4-chlorophenyl)-1,3,4-oxadiazol-2-yl)methyl)pyridazin-3(2H)-one,
2-((5-(3-methoxyphenyl)-1,3,4-oxadiazol-2-yl)methyl)-6-methylpyridazin-3(2H)-one,
6-methyl-2-((5-(4-nitrophenyl)-1,3,4-oxadiazol-2-yl)methyl)pyridazin-3(2H)-one,
5,6-diethyl-2-((5-isopropyl-1,3,4-oxadiazol-2-yl)methyl)-3-oxo-2,3-dihydropyridazine-4-carbonitrile,
2-((5-(4-bromophenyl)-1,3,4-oxadiazol-2-yl)methyl)-5,6-diethyl-3-oxo-2,3-dihydropyridazine-4-carbonitrile,
4,5-dichloro-2-((5-(4-nitrophenyl)-1,3,4-oxadiazol-2-yl)methyl)pyridazin-3(2H)-one,
4,5-dichloro-2-((5-(3,4,5-trimethoxyphenyl)-1,3,4-oxadiazol-2-yl)methyl)pyridazin-3(2H)-one,
2-((5-cyclopropyl-1,3,4-oxadiazol-2-yl)methyl)-5,6-diethyl-3-oxo-2,3-dihydropyridazine-4-carbonitrile,
6-cyclopropyl-2-((5-ethyl-1,3,4-oxadiazol-2-yl)methyl)-4-(trifluoromethyl)pyridazin-3(2H)-one,
2-((5-(tert-butyl)-1,3,4-oxadiazol-2-yl)methyl)-6-cyclopropyl-4-(trifluoromethyl)pyridazin-3(2H)-one,
6-cyclopropyl-2-((5-methyl-1,3,4-oxadiazol-2-yl)methyl)-4-(trifluoromethyl)pyridazin-3(2H)-one,
6-cyclopropyl-2((5-cyclopropyl-1,3,4-oxadiazol-2-yl)methyl)-4-(trifluoromethyl)pyridazin-3(2H)-one,
5,6-dimethyl-2-((5-(4-nitrophenyl)-1,3,4-oxadiazol-2-yl)methyl)-3-oxo-2,3-dihydropyridazine-4-carbonitrile,
5,6-dimethyl-3-oxo-2-((5-(3,4,5-trimethoxyphenyl)-1,3,4-oxadiazol-2-yl)methyl)-2,3-dihydropyridazine-4-carbonitrile,
2-((5-(4-bromophenyl)-1,3,4-oxadiazol-2-yl)methyl)-6-cyclopropyl-4-(trifluoromethyl)pyridazin-3(2H)-one,
2-((5-(3-bromophenyl)-1,3,4-oxadiazol-2-yl)methyl)-6-cyclopropyl-4-(trifluoromethyl)pyridazin-3 (2H)-one, 6-cyclopropyl-4-(trifluoromethyl)-2-((5-(3,4,5-trimethoxyphenyl)-1,3,4-oxadiazol-2-yl)methyl)pyridazin-3 (2H)-one,
2-((5-(3-bromophenyl)-1,3,4-oxadiazol-2-yl)methyl)-4,5-dichloropyridazin-3 (2H)-one,
4,5-dichloro-2-((5-(4-methoxyphenyl)-1,3,4-oxadiazol-2-yl)methyl)pyridazin-3 (2H)-one,
2-((5-(5-bromofuran-2-yl)-1,3,4-oxadiazol-2-yl)methyl)-4,5-dichloropyridazin-3 (2H)-one,
5,6-dimethyl-3-oxo-2-((5-phenyl-1,3,4-oxadiazol-2-yl)methyl)-2,3-dihydropyridazine-4-carbonitrile,
2-((5-(4-methoxyphenyl)-1,3,4-oxadiazol-2-yl)methyl)-5,6-dimethyl-3-oxo-2,3-dihydropyridazine-4-carbonitrile,
2-((5-(4-bromophenyl)-1,3,4-oxadiazol-2-yl)methyl)-4,5-dichloropyridazin-3 (2H)-one,
4,5-dichloro-2-((5-(thiophen-2-yl)-1,3,4-oxadiazol-2-yl)methyl)pyridazin-3 (2H)-one,
2-((5-(2-bromophenyl)-1,3,4-oxadiazol-2-yl)methyl)-4,5-dichloropyridazin-3(2H)-one.

2. A compound as claimed in claim 1, or a pharmaceutically acceptable salt thereof, wherein $R^4$ represents F or $C_1$ alkyl optionally substituted by one or more F.

3. A compound as claimed in claim 1, or a pharmaceutically acceptable salt thereof, wherein W represents —CH$_2$—.

4. A compound as claimed in claim 1, or a pharmaceutically acceptable salt thereof, wherein Y represents phenyl optionally substituted by one or more groups independently selected from $G^{1c}$.

5. A compound as claimed in claim 1, or a pharmaceutically acceptable salt thereof, wherein $G^{1c}$ represents halo, $R^{za}$, —NO$_2$ or —OR$^{m2}$.

6. A compound as claimed in claim 1, or a pharmaceutically acceptable salt thereof, wherein Z represents O.

7. A compound as claimed in claim 1, or a pharmaceutically acceptable salt thereof, wherein:
$R^1$ represents H, halo, $R^{a1}$, —CN, —C(O)$R^{b1}$, —C(O)OR$^{e1}$, —S(O)$_2$R$^{f1}$ or —NO$_2$; and
$R^{a1}$, $R^{b1}$, $R^{e1}$ and $R^{f1}$ represents $C_{1-6}$ alkyl optionally substituted by one or more F.

8. A compound as claimed in claim 1, or a pharmaceutically acceptable salt thereof, wherein $R^2$ represents halo.

9. A compound as claimed in claim 1, or a pharmaceutically acceptable salt thereof, wherein $R^3$ represents H.

10. A compound as claimed in claim 1, or a pharmaceutically acceptable salt thereof, wherein:
both of $R^1$ and $R^2$ represent Cl; and/or
$R^3$ represents H.

11. A method of treating cancer, wherein the cancer is selected from pharyngeal squamous cell carcinoma, colorectal carcinoma, epidermoid (skin) carcinoma and lung carcinoma comprising administering to a patient in need thereof a therapeutically effective amount of a compound, wherein the compound is represented by formula I

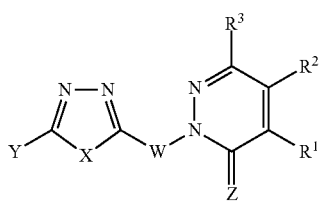

(I)

or a pharmaceutically acceptable salt thereof, wherein:
W represents $C_1$ alkylene optionally substituted by one or more groups independently selected from $R^4$;
X represents O;
Y represents $C_{1-6}$ alkyl optionally substituted by one or more groups independently selected from $G^{1a}$, $C_{2-6}$ alkenyl optionally substituted by one or more groups independently selected from $G^{1a}$, $C_{2-6}$ alkynyl optionally substituted by one or more groups independently selected from $G^{1a}$, heterocycloalkyl optionally substituted by one or more groups independently selected from $G^{1b}$, aryl optionally substituted by one or more groups independently selected from $G^{1c}$, or heteroaryl optionally substituted by one or more groups independently selected from $G^{1d}$;
Z represents O, S or NR$^5$;
$R^1$ represents H, halo, $R^{a1}$, —CN, —C($Q^{a1}$)$R^{b1}$, —C($Q^{b1}$)N($R^{c1}$)$R^{d1}$, —C($Q^{c1}$)OR$^{e1}$, —S(O)$_n$R$^{f1}$, —S(O)$_p$N($R^{g1}$)$R^{h1}$, —S(O)$_p$OR$^{i1}$ or —NO$_2$;
$R^2$ represents H, halo, —CN or —N$_3$;
$R^3$ represents H, halo or $R^{j1}$;
$R^4$ represents halo, $C_{1-6}$ alkyl optionally substituted by one or more groups independently selected from $G^{1e}$, $C_{2-6}$ alkenyl optionally substituted by one or more groups independently selected from $G^{1e}$, or $C_{2-6}$ alkynyl optionally substituted by one or more groups independently selected from $G^{1e}$;
$R^5$ represents H, $R^{k1}$, —OR$^{l1}$ or —N(R$^{m1}$)R$^{n1}$;
$Q^{a1}$ to $Q^{c1}$ each independently represents =O, =S, =NR$^{o1}$ or =N(OR$^{p1}$);
each $R^{a1}$, $R^{f1}$, $R^{j1}$ and $R^{k1}$ independently represents $C_{1-6}$ alkyl optionally substituted by one or more groups independently selected from $G^{2a}$, $C_{2-6}$ alkenyl optionally substituted by one or more groups independently selected from $G^{2a}$, $C_{2-6}$ alkynyl optionally substituted by one or more groups independently selected from $G^{2a}$, or heterocycloalkyl optionally substituted by one or more groups independently selected from $G^{2b}$;
each $R^{b1}$, $R^{c1}$, $R^{d1}$, $R^{e1}$, $R^{g1}$, $R^{h1}$, $R^{i1}$, $R^{l1}$, $R^{m1}$, $R^{n1}$, $R^{o1}$ and $R^{p1}$ independently represents H, $C_{1-6}$ alkyl optionally substituted by one or more groups independently selected from $G^{2a}$, $C_{2-6}$ alkenyl optionally substituted by one or more groups independently selected from $G^{2a}$, $C_{2-6}$ alkynyl optionally substituted by one or more groups independently selected from $G^{2a}$, or heterocycloalkyl optionally substituted by one or more groups independently selected from $G^{2b}$;
or any two $R^{c1}$ and $R^{d1}$, $R^{g1}$ and $R^{h1}$ and/or $R^{m1}$ and $R^{n1}$ are linked together to form, along with the nitrogen atom to which they are attached, a 3- to 6-membered ring, which ring optionally contains one further heteroatom and which ring optionally is substituted by one or more groups independently selected from halogen, $C_{1-3}$ alkyl optionally substituted by one or more halogens, $C_{2-3}$ alkenyl optionally substituted by one or more halogens, $C_{2-3}$ alkynyl optionally substituted by one or more halogens, and =O;
each $G^{1a}$, $G^{1b}$, $G^{1c}$ and $G^{1d}$ represent halogen, $R^{A2}$, —CN, -A$^{a1}$-C($Q^{a2}$)R$^{b2}$, -A$^{b1}$-C($Q^{b2}$)N(R$^{c2}$)R$^{d2}$, -A$^{c1}$-C($Q^{c2}$)OR$^{e2}$, -A$^{d1}$-S(O)$_q$R$^{f2}$, -A$^{e1}$-S(O)$_q$C(O)R$^{g2}$, -A$^{f1}$-S(O)$_q$N(R$^{h2}$)R$^{i2}$, -A$^{g1}$-S(O)$_q$OR$^{j2}$, —N$_3$, —N(R$^{k2}$)R$^{l2}$, —N(H)CN, —NO$_2$, —OR$^{m2}$, —SR$^{n2}$ or =Q$^{d2}$;
A$^{a1}$ to A$^{g1}$ each independently represents a single bond, —N(R$^6$)—, —C(Q$^{e2}$)N(R$^7$)— or —O—;
Q$^{a2}$ to Q$^{e2}$ each independently represents =O, =S, =NR$^{o2}$ or =N(OR$^{p2}$);

each $R^6$ and $R^7$ independently represents H, $C_{1-6}$ alkyl optionally substituted by one or more F, $C_{2-6}$ alkenyl optionally substituted by one or more F, or $C_{2-6}$ alkynyl optionally substituted by one or more F;

each $R^{a2}$ and $R^{f2}$ independently represents $C_{1-6}$ alkyl optionally substituted by one or more groups independently selected from $G^{3a}$, $C_{2-6}$ alkenyl optionally substituted by one or more groups independently selected from $G^{3a}$, $C_{2-6}$ alkynyl optionally substituted by one or more groups independently selected from $G^{3a}$, or heterocycloalkyl optionally substituted by one or more groups independently selected from $G^{3b}$;

each $R^{b2}$, $R^{c2}$, $R^{d2}$, $R^{e2}$, $R^{g2}$, $R^{h2}$, $R^{i2}$, $R^{j2}$, $R^{k2}$, $R^{l2}$, $R^{m2}$, $R^{n2}$, $R^{o2}$ and $R^{p2}$ independently represents H, $C_{1-6}$ alkyl optionally substituted by one or more groups independently selected from $G^{3a}$, $C_{2-6}$ alkenyl optionally substituted by one or more groups independently selected from $G^{3a}$, $C_{2-6}$ alkynyl optionally substituted by one or more groups independently selected from $G^{3a}$, or heterocycloalkyl optionally substituted by one or more groups independently selected from $G^{3b}$; or any two $R^{c2}$ and $R^{d2}$, $R^{h2}$ and $R^{i2}$ and/or $R^{k2}$ and $R^{l2}$ are linked together to form, along with the nitrogen atom to which they are attached, a 3- to 6-membered ring, which ring optionally contains one further heteroatom and which ring optionally is substituted by one or more groups independently selected from halogen, $C_{1-3}$ alkyl optionally substituted by one or more halogens, $C_{2-3}$ alkenyl optionally substituted by one or more halogens, $C_{2-3}$ alkynyl optionally substituted by one or more halogens, and =O;

each $G^{1e}$ independently represents halo, $R^{a2}$, —CN, —N($R^{a3}$)$R^{b3}$, —O$R^{c3}$ or —S$R^{d3}$;

$R^{a3}$, $R^{b3}$, $R^{c3}$ and $R^{d3}$ each independently represents H, $C_{1-6}$ alkyl optionally substituted by one or more F, $C_{2-6}$ alkenyl optionally substituted by one or more F, or $C_{2-6}$ alkynyl optionally substituted by one or more F;

or $R^{a3}$ and $R^{b3}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, $C_{2-3}$ alkenyl optionally substituted by one or more fluoro, $C_{2-3}$ alkynyl optionally substituted by one or more fluoro, and =O;

each $G^{2a}$ and $G^{2b}$ independently represents halo, —CN, —N($R^{a4}$)$R^{b4}$, —O$R^{c4}$, —S$R^{d4}$ or =O;

each $R^{a4}$, $R^{b4}$, $R^{c4}$ and $R^{d4}$ independently represents H, $C_{1-6}$ alkyl optionally substituted by one or more fluoro, $C_{2-6}$ alkenyl optionally substituted by one or more fluoro, or $C_{2-6}$ alkynyl optionally substituted by one or more fluoro;

or $R^{a4}$ and $R^{b4}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, $C_{2-3}$ alkenyl optionally substituted by one or more fluoro, $C_{2-3}$ alkynyl optionally substituted by one or more fluoro, and =O;

each $G^{3a}$ and $G^{3b}$ independently represents halo, —CN, —N($R^{a5}$)$R^{b5}$, —O$R^{c5}$, —S$R^{d5}$ or =O;

each $R^{a5}$, $R^{b5}$, $R^{c5}$ and $R^{d5}$ independently represents H, $C_{1-6}$ alkyl optionally substituted by ONE OR MORE FLUORO, $C_{2-6}$ ALKENYL OPTIONALLY SUBSTITUTED BY ONE OR MORE FLUORO, OR $C_{2-6}$ ALKYNYL optionally substituted by one or more fluoro;

or $R^{a5}$ and $R^{b5}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, $C_{2-3}$ alkenyl optionally substituted by one or more fluoro, $C_{2-3}$ alkynyl optionally substituted by one or more fluoro, and =O;

each n independently represents 0, 1 or 2,
each p independently represents 1 or 2, and
each q independently represents 1 or 2.

12. A pharmaceutical composition comprising a compound, and optionally one or more pharmaceutically acceptable adjuvant, diluent and/or carrier, wherein the compound is represented by formula I

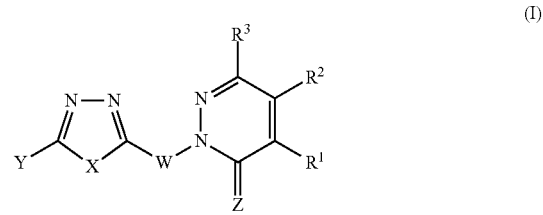

(I)

or a pharmaceutically acceptable salt thereof, wherein:

W represents $C_1$ alkylene optionally substituted by one or more groups independently selected from $R^4$;

X represents O;

Y represents $C_{1-6}$ alkyl optionally substituted by one or more groups independently selected from $G^{1a}$, $C_{2-6}$ alkenyl optionally substituted by one or more groups independently selected from $G^{1a}$, $C_{2-6}$ alkynyl optionally substituted by one or more groups independently selected from $G^{1a}$, heterocycloalkyl optionally substituted by one or more groups independently selected from $G^{1b}$, aryl optionally substituted by one or more groups independently selected from $G^{1c}$, or heteroaryl optionally substituted by one or more groups independently selected from $G^{1d}$;

Z represents O, S or N$R^5$;

$R^1$ represents H, halo, $R^{a1}$, —CN, —C($Q^{a1}$)$R^{b1}$, —C($Q^{b1}$)N($R^{c1}$)$R^{d1}$, —C($Q^{c1}$)O$R^{e1}$, —S(O)$_n$$R^{f1}$, —S(O)$_p$N($R^{g1}$)$R^{h1}$, —S(O)$_p$O$R^{i1}$ or —NO$_2$;

$R^2$ represents H, halo, —CN or —N$_3$;

$R^3$ represents H, halo or $R^{j1}$;

$R^4$ represents halo, $C_{1-6}$ alkyl optionally substituted by one or more groups independently selected from $G^{1e}$, $C_{2-6}$ alkenyl optionally substituted by one or more groups independently selected from $G^{1e}$, or $C_{2-6}$ alkynyl optionally substituted by one or more groups independently selected from $G^{1e}$;

$R^5$ represents H, $R^{k1}$, —O$R^{l1}$ or —N($R^{m1}$)$R^{n1}$;

$Q^{a1}$ to $Q^{c1}$ each independently represents =O, =S, =N$R^{o1}$ or =N(O$R^{p1}$);

each $R^{a1}$, $R^{j1}$, $R^{j1}$ and $R^{k1}$ independently represents $C_{1-6}$ alkyl optionally substituted by one or more groups independently selected from $G^{2a}$, $C_{2-6}$ alkenyl optionally substituted by one or more groups independently selected from $G^{2a}$, $C_{2-6}$ alkynyl optionally substituted by one or more groups independently selected from $G^{2a}$, or heterocycloalkyl optionally substituted by one or more groups independently selected from $G^{2b}$;

each $R^{b1}$, $R^{c1}$, $R^{d1}$, $R^{e1}$, $R^{g1}$, $R^{h1}$, $R^{i1}$, $R^{j1}$, $R^{m1}$, $R^{n1}$, $R^{o1}$ and $R^{p1}$ independently represents H, $C_{1-6}$ alkyl optionally substituted by one or more groups independently selected from $G^{2a}$, $C_{2-6}$ alkenyl optionally substituted by one or more groups independently selected from $G^{2a}$, $C_{2-6}$ alkynyl optionally substituted by one or more groups independently selected from $G^{2a}$, or heterocycloalkyl optionally substituted by one or more groups independently selected from $G^{2b}$;

or any two $R^{c1}$ and $R^{d1}$, $R^{g1}$ and $R^{h1}$ and/or $R^{m1}$ and $R^{n1}$ are linked together to form, along with the nitrogen atom to which they are attached, a 3- to 6-membered ring, which ring optionally contains one further heteroatom and which ring optionally is substituted by one or more groups independently selected from halogen, $C_{1-3}$ alkyl optionally substituted by one or more halogens, $C_{2-3}$ alkenyl optionally substituted by one or more halogens, $C_{2-3}$ alkynyl optionally substituted by one or more halogens, and =O;

each $G^{1a}$, $G^{1b}$, $G^{1c}$ and $G^{1d}$ represent halogen, $R^{a2}$, —CN, $-A^{a1}-C(Q^{a2})R^{b2}$, $-A^{b1}-C(Q^{b2})N(R^{c2})R^{d2}$, $-A^{c1}-C(Q^{c2})OR^{e2}$, $-A^{d1}-S(O)_qR^{f2}$, $-A^{e1}-S(O)_qC(O)R^{g2}$, $-A^{f1}-S(O)_qN(R^{h2})R^{i2}$, $-A^{g1}-S(O)_qOR^{j2}$, —$N_3$, —$N(R^{k2})R^{l2}$, —N(H)CN, —$NO_2$, —$OR^{m2}$, —$SR^{n2}$ or =$Q^{d2}$;

$A^{a1}$ to $A^{g1}$ each independently represents a single bond, —$N(R^6)$—, —$C(Q^{e2})N(R^7)$— or —O—;

$Q^{a2}$ to $Q^{e2}$ each independently represents =O, =S, =$NR^{o2}$ or =$N(OR^{p2})$;

each $R^6$ and $R^7$ independently represents H, $C_{1-6}$ alkyl optionally substituted by one or more F, $C_{2-6}$ alkenyl optionally substituted by one or more F, or $C_{2-6}$ alkynyl optionally substituted by one or more F;

each $R^{a2}$ and $R^{f2}$ independently represents $C_{1-6}$ alkyl optionally substituted by one or more groups independently selected from $G^{3a}$, $C_{2-6}$ alkenyl optionally substituted by one or more groups independently selected from $G^{3a}$, $C_{2-6}$ alkynyl optionally substituted by one or more groups independently selected from $G^{3a}$, or heterocycloalkyl optionally substituted by one or more groups independently selected from $G^{3b}$;

each $R^{b2}$, $R^{c2}$, $R^{d2}$, $R^{e2}$, $R^{g2}$, $R^{h2}$, $R^{i2}$, $R^{j2}$, $R^{k2}$, $R^{l2}$, $R^{m2}$, $R^{n2}$, $R^{o2}$ and $R^{p2}$ independently represents H, $C_{1-6}$ alkyl optionally substituted by one or more groups independently selected from $G^{3a}$, $C_{2-6}$ alkenyl optionally substituted by one or more groups independently selected from $G^{3a}$, $C_{2-6}$ alkynyl optionally substituted by one or more groups independently selected from $G^{3a}$, or heterocycloalkyl optionally substituted by one or more groups independently selected from $G^{3b}$; or any two $R^{c2}$ and $R^{d2}$, $R^{h2}$ and $R^{i2}$ and/or $R^{k2}$ and $R^{l2}$ are linked together to form, along with the nitrogen atom to which they are attached, a 3- to 6-membered ring, which ring optionally contains one further heteroatom and which ring optionally is substituted by one or more groups independently selected from halogen, $C_{1-3}$ alkyl optionally substituted by one or more halogens, $C_{2-3}$ alkenyl optionally substituted by one or more halogens, $C_{2-3}$ alkynyl optionally substituted by one or more halogens, and =O;

each $G^{1e}$ independently represents halo, $R^{a2}$, —CN, —$N(R^{a3})R^{b3}$, —$OR^{c3}$ or —$SR^{d3}$;

$R^{a3}$, $R^{b3}$, $R^{c3}$ and $R^{d3}$ each independently represents H, $C_{1-6}$ alkyl optionally substituted by one or more F, $C_{2-6}$ alkenyl optionally substituted by one or more F, or $C_{2-6}$ alkynyl optionally substituted by one or more F;

or $R^{a3}$ and $R^{b3}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, $C_{2-3}$ alkenyl optionally substituted by one or more fluoro, $C_{2-3}$ alkynyl optionally substituted by one or more fluoro, and =O;

each $G^{2a}$ and $G^{2b}$ independently represents halo, —CN, —$N(R^{a5})R^{b5}$, —$OR^{c5}$, —$SR^{d5}$ or =O;

each $R^{a4}$, $R^{b4}$, $R^{c4}$ and $R^{d4}$ independently represents H, $C_{1-6}$ alkyl optionally substituted by one or more fluoro, $C_{2-6}$ alkenyl optionally substituted by one or more fluoro, or $C_{2-6}$ alkynyl optionally substituted by one or more fluoro;

or $R^{a4}$ and $R^{b4}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, $C_{2-3}$ alkenyl optionally substituted by one or more fluoro, $C_{2-3}$ alkynyl optionally substituted by one or more fluoro, and =O;

each $G^{3a}$ and $G^{3b}$ independently represents halo, —CN, —$N(R^{a5})R^{b5}$, —$OR^{c5}$, —$SR^{d5}$ or =O;

each $R^{a5}$, $R^{b5}$, $R^{c5}$ and $R^{d5}$ independently represents H, $C_{1-6}$ alkyl optionally substituted by one or more fluoro, $C_{2-6}$ alkenyl optionally substituted by one or more fluoro, or $C_{2-6}$ alkynyl optionally substituted by one or more fluoro;

or $R^{a5}$ and $R^{b5}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, $C_{2-3}$ alkenyl optionally substituted by one or more fluoro, $C_{2-3}$ alkynyl optionally substituted by one or more fluoro, and =O;

each n independently represents 0, 1 or 2,
each p independently represents 1 or 2, and
each q independently represents 1 or 2.

13. A combination product comprising:

(I) a pharmaceutical formulation as defined in claim 12; and (II) one or more other therapeutic agent that is useful in the treatment of cancer, wherein the cancer is selected from the group consisting of pharyngeal squamous cell carcinoma, colorectal carcinoma, epidermoid (skin) carcinoma and lung carcinoma, wherein each of components (I) and (II) is formulated in admixture, optionally with one or more a pharmaceutically-acceptable adjuvant, diluent or carrier, wherein the compound is represented by formula I

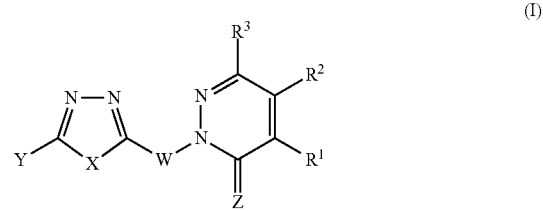

or a pharmaceutically acceptable salt thereof, wherein:

W represents $C_1$ alkylene optionally substituted by one or more groups independently selected from $R^4$;

X represents O;

Y represents $C_{1-6}$ alkyl optionally substituted by one or more groups independently selected from $G^{1a}$, $C_{2-6}$ alkenyl optionally substituted by one or more groups independently selected from $G^{1a}$, $C_{2-6}$ alkynyl optionally substituted by one or more groups independently selected from $G^{1a}$, heterocycloalkyl optionally substituted by one or more groups independently selected from $G^{1b}$, aryl optionally substituted by one or more groups independently selected from $G^{1c}$, or heteroaryl optionally substituted by one or more groups independently selected from $G^{1d}$;

Z represents O, S or $NR^5$;

$R^1$ represents H, halo, $R^{a1}$, —CN, —C($Q^{a1}$)$R^{b1}$, —C($Q^{b1}$)N($R^{c1}$)$R^{d1}$, —C($Q^{c1}$)$OR^{e1}$, —S(O)$_n$$R^{f1}$, —S(O)$_p$N($R^{g1}$)$R^{h1}$, —S(O)$_p$$OR^{i1}$ or —$NO_2$;

$R^2$ represents H, halo, —CN or —$N_3$;

$R^3$ represents H, halo or $R^{j1}$;

$R^4$ represents halo, $C_{1-6}$ alkyl optionally substituted by one or more groups independently selected from $G^{1e}$, $C_{2-6}$ alkenyl optionally substituted by one or more groups independently selected from $G^{1e}$, or $C_{2-6}$ alkynyl optionally substituted by one or more groups independently selected from $G^{1e}$;

$R^5$ represents H, $R^{k1}$, —$OR^{l1}$ or —N($R^{m1}$)$R^{n1}$;

$Q^{a1}$ to $Q^{c1}$ each independently represents =O, =S, =$NR^{o1}$ or =N($OR^{p1}$);

each $R^{a1}$, $R^{f1}$, $R^{j1}$ and $R^{k1}$ independently represents $C_{1-6}$ alkyl optionally substituted by one or more groups independently selected from $G^{2a}$, $C_{2-6}$ alkenyl optionally substituted by one or more groups independently selected from $G^{2a}$, $C_{2-6}$ alkynyl optionally substituted by one or more groups independently selected from $G^{2a}$, or heterocycloalkyl optionally substituted by one or more groups independently selected from $G^{2b}$;

each $R^{b1}$, $R^{c1}$, $R^{d1}$, $R^{e1}$, $R^{g1}$, $R^{h1}$, $R^{i1}$, $R^{l1}$, $R^{m1}$, $R^{n1}$, $R^{o1}$ and $R^{p1}$ independently represents H, $C_{1-6}$ alkyl optionally substituted by one or more groups independently selected from $G^{2a}$, $C_{2-6}$ alkenyl optionally substituted by one or more groups independently selected from $G^{2a}$, $C_{2-6}$ alkynyl optionally substituted by one or more groups independently selected from $G^{2a}$, or heterocycloalkyl optionally substituted by one or more groups independently selected from $G^{2b}$, or any two $R^{c1}$ and $R^{d1}$, $R^{g1}$ and $R^{h1}$ and/or $R^{m1}$ and $R^{n1}$ are linked together to form, along with the nitrogen atom to which they are attached, a 3- to 6-membered ring, which ring optionally contains one further heteroatom and which ring optionally is substituted by one or more groups independently selected from halogen, $C_{1-3}$ alkyl optionally substituted by one or more halogens, $C_{2-3}$ alkenyl optionally substituted by one or more halogens, $C_{2-3}$ alkynyl optionally substituted by one or more halogens, and =O;

each $G^{1a}$, $G^{1b}$, $R^{1c}$ and $G^{1d}$ represent halogen, $R^{a2}$, —CN, -$A^a$-C($Q^{a2}$)$R^{b2}$, -$A^{b1}$-C($Q^{b2}$)N($R^{c2}$)$R^{d2}$, -$A^{c1}$-C($Q^{c2}$)$OR^{e2}$, -$A^{d1}$-S(O)$_q$$R^{f2}$, -$A^{e1}$-S(O)$_q$C(O)$R^{g2}$, -$A^{f1}$-S(O)$_q$N($R^{h2}$)$R^{i2}$, -$A^{g1}$-S(O)$_q$$OR^{j2}$, —$N_3$, —N($R^{k2}$)$R^{l2}$, —N(H)CN, —$NO_2$, —$OR^{m2}$, —$SR^{n2}$ or =$Q^{d2}$;

$A^{a1}$ to $A^{g1}$ each independently represents a single bond, —N($R^6$)—, —C($Q^{e2}$)N($R^7$)— or —O—;

$Q^{a2}$ to $Q^{e2}$ each independently represents =O, =S, =$NR^{o2}$ or =N($OR^{p2}$);

each $R^6$ and $R^7$ independently represents H, $C_{1-6}$ alkyl optionally substituted by one or more F, $C_{2-6}$ alkenyl optionally substituted by one or more F, or $C_{2-6}$ alkynyl optionally substituted by one or more F;

each $R^{a2}$ and $R^{f2}$ independently represents $C_{1-6}$ alkyl optionally substituted by one or more groups independently selected from $G^{3a}$, $C_{2-6}$ alkenyl optionally substituted by one or more groups independently selected from $G^{3a}$, $C_{2-6}$ alkynyl optionally substituted by one or more groups independently selected from $G^{3a}$, or heterocycloalkyl optionally substituted by one or more groups independently selected from $G^{3b}$;

each $R^{b2}$, $R^{c2}$, $R^{d2}$, $R^{e2}$, $R^{g2}$, $R^{h2}$, $R^{i2}$, $R^{j2}$, $R^{k2}$, $R^{l2}$, $R^{m2}$, $R^{n2}$, $R^{o2}$ and $R^{p2}$ independently represents H, $C_{1-6}$ alkyl optionally substituted by one or more groups independently selected from $G^{3a}$, $C_{2-6}$ alkenyl optionally substituted by one or more groups independently selected from $G^{3a}$, $C_{2-6}$ alkynyl optionally substituted by one or more groups independently selected from $G^{3a}$, or heterocycloalkyl optionally substituted by one or more groups independently selected from $G^{3b}$; or any two $R^{c2}$ and $R^{d2}$, $R^{h2}$ and $R^{i2}$ and/or $R^{k2}$ and $R^{l2}$ are linked together to form, along with the nitrogen atom to which they are attached, a 3- to 6-membered ring, which ring optionally contains one further heteroatom and which ring optionally is substituted by one or more groups independently selected from halogen, $C_{1-3}$ alkyl optionally substituted by one or more halogens, $C_{2-3}$ alkenyl optionally substituted by one or more halogens, $C_{2-3}$ alkynyl optionally substituted by one or more halogens, and =O;

each $G^{1e}$ independently represents halo, $R^{a2}$, —CN, —N($R^{a3}$)$R^{b3}$, —$OR^{c3}$ or —$SR^{d3}$;

$R^{a3}$, $R^{b3}$, $R^{c3}$ and $R^{d3}$ each independently represents H, $C_{1-6}$ alkyl optionally substituted by one or more F, $C_{2-6}$ alkenyl optionally substituted by one or more F, or $C_{2-6}$ alkynyl optionally substituted by one or more F;

or $R^{a3}$ and $R^{b3}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, $C_{2-3}$ alkenyl optionally substituted by one or more fluoro, $C_{2-3}$ alkynyl optionally substituted by one or more fluoro, and =O;

each $G^{2a}$ and $G^{2b}$ independently represents halo, —CN, —N($R^{a4}$)$R^{b4}$, —$OR^{c4}$, —$SR^{d4}$ or =O;

each $R^{a4}$, $R^{b4}$, $R^{c4}$ and $R^{d4}$ independently represents H, $C_{1-6}$ alkyl optionally substituted by one or more fluoro, $C_{2-6}$ alkenyl optionally substituted by one or more fluoro, or $C_{2-6}$ alkynyl optionally substituted by one or more fluoro;

or $Ra^{a4}$ and $R^{b4}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, $C_{2-3}$ alkenyl optionally substituted by one or more fluoro, $C_{2-3}$ alkynyl optionally substituted by one or more fluoro, and =O;

each $G^{3a}$ and $G^{3b}$ independently represents halo, —CN, —N($R^{a5}$)$R^{b5}$, —$OR^{c5}$, —$SR^{d5}$ or =O;

each $R^{a5}$, $R^{b5}$, $R^{c5}$ and $R^{d5}$ independently represents H, $C_{1-6}$ alkyl optionally substituted by one or more fluoro, $C_{2-6}$ alkenyl optionally substituted by one or more fluoro, or $C_{2-6}$ alkynyl optionally substituted by one or more fluoro;

or $R^{a5}$ and $R^{b5}$ are linked together to form, along with the nitrogen atom to which they are attached, a 3- to 6-membered ring, which ring optionally contains one further heteroatom and which ring optionally is substituted by one or more groups independently selected from fluoro, $C_{1-3}$ alkyl optionally substituted by one or more fluoro, $C_{2-3}$ alkenyl optionally substituted by one or more fluoro, $C_{2-3}$ alkynyl optionally substituted by one or more fluoro, and =O;

each n independently represents 0, 1 or 2,
each p independently represents 1 or 2, and
each q independently represents 1 or 2.

14. A kit-of-parts comprising:
(a) a pharmaceutical formulation as defined in claim 12; and
(b) one or more other therapeutic agent that is useful in the treatment of cancer, wherein the cancer is selected from the group consisting of pharyngeal squamous cell carcinoma, colorectal carcinoma, epidermoid (skin) carcinoma and lung carcinoma, and wherein the one or more other therapeutic agent is optionally in admixture with one or more pharmaceutically-acceptable adjuvant, diluent or carrier, which components (a) and (b) are each provided in a form that is suitable for administration in conjunction with the other.

15. A process for the preparation of a compound as defined in claim 1, which process comprises:
(i) reaction of a compound of formula II

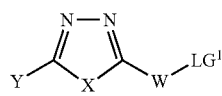

(II)

wherein W, X and Y are as defined in claim 1 and $LG^1$ represents a suitable leaving group, with a compound of formula III

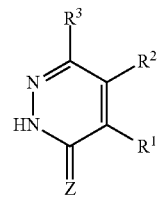

(III)

wherein $R^1$ to $R^3$ and Z are as defined in claim 1, in the presence of a suitable base and in the presence of a suitable solvent; or (ii) reaction of a compound of formula IV

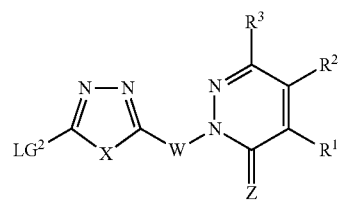

(IV)

wherein W, X, Z and $R^1$ to $R^3$ are as defined in claim 1 and $LG^2$ represents a suitable leaving group, with a compound of formula V $Y-B^1$       (V)

wherein Y is as defined in claim 1 and $B^1$ represents a group suitable for participating in a coupling reaction in the presence of a suitable catalyst and in the presence of a suitable solvent.

\* \* \* \* \*